United States Patent

Solen et al.

[11] Patent Number: 6,043,871
[45] Date of Patent: Mar. 28, 2000

[54] SYSTEM AND METHOD FOR MEASURING BLOOD PLATELET FUNCTION

[75] Inventors: Kenneth A. Solen, Orem; S. Fazal Mohammad, Salt Lake City, both of Utah

[73] Assignee: Brigham Young University, Provo, Utah

[21] Appl. No.: 09/033,919

[22] Filed: Mar. 3, 1998

Related U.S. Application Data

[60] Provisional application No. 60/039,755, Mar. 3, 1997.

[51] Int. Cl.⁷ .................................................. G01N 33/48
[52] U.S. Cl. ............................... 356/39; 356/427; 435/13; 436/69
[58] Field of Search ...................... 356/336, 338, 356/343, 39–41; 250/574; 128/633; 435/13; 600/577, 368

[56] References Cited

U.S. PATENT DOCUMENTS

| | | |
|---|---|---|
| 3,989,382 | 11/1976 | Kent et al. . |
| 4,066,360 | 1/1978 | Breddin et al. . |
| 4,135,818 | 1/1979 | Kent et al. . |
| 4,284,412 | 8/1981 | Hansen et al. .................. 435/7.24 |
| 4,319,194 | 3/1982 | Cardinal et al. . |
| 4,601,080 | 2/1997 | Oppenheimer . |
| 5,293,210 | 3/1994 | Berndt . |
| 5,325,295 | 6/1994 | Fratantoni et al. . |
| 5,351,686 | 10/1994 | Steuer et al. . |
| 5,372,136 | 12/1994 | Steuer et al. . |
| 5,428,443 | 6/1995 | Kitamura et al. ................. 356/336 |
| 5,456,253 | 10/1995 | Steuer et al. . |
| 5,523,238 | 6/1996 | Varon et al. . |
| 5,563,041 | 10/1996 | Reers . |
| 5,569,590 | 10/1996 | Speck . |
| 5,796,480 | 8/1998 | Igushi ................................. 356/336 |
| 5,907,399 | 5/1999 | Shirasawa et al. ................ 356/336 |

OTHER PUBLICATIONS http://www.erols.com/chronlog Feb. 21, 1998.
"Critical Evaluation of Platelet Aggregation in Whole Human Blood", Riess H., 1985.
"Size Distribution Measurements of Microaggregates in Stored Blood", Reynolds, L., 1979.
"Thrombotic Events on Grafted Polyacrylanide–Silastic Surfaces as Studied in a Baboon", Hoffman, A, 1981.
"Characterization of Blood Microemboli Associated With Ex Vivo Left Ventricular Assist Devices in a Bovine Model", Solen, K., 1989.
"Markers of Thromboembloization in a Bovine Ex Vivo Left Ventricular Assist Device Model", Solen, K., 1994.
"Aggregation of Blood Platelets by Adenosine Diphosphate and Its Reversal", Born, G., 1962.

Primary Examiner—Frank G. Font
Assistant Examiner—Layla Lauchman
Attorney, Agent, or Firm—Clayton, Howarth & Cannon, P.C.

[57] ABSTRACT

An instrument is described for measuring the platelet aggregation in whole blood in response to standard aggregating agents. The instrument is designed to be used in the clinical laboratory to evaluate the functional status of platelets in blood samples drawn from patients suspected of abnormal platelet function, or in a research laboratory to evaluate the effectiveness of platelet agonists or antiplatelet agents. The measurement is based on the scattering of light in the blood sample and does not require separation of erythrocytes from blood and therefore helps minimize the need for handling of blood by the laboratory personnel. The instrument converts the light-scattering data to provide the number and average size of the aggregates per unit volume at various times during the process of aggregation.

50 Claims, 11 Drawing Sheets

SYSTEM AND METHOD FOR MEASURING BLOOD PLATELET FUNCTION

This application claims the benefit of U.S. Provisional Application No. 60/039,755 filed Mar. 3, 1997.

BACKGROUND

1. The Field of the Invention

This invention relates to devices used to analyze blood. More particularly, the present invention relates to devices-used to assess platelet function in blood.

2. The Background Art

Platelets are among the smallest corpuscular components of human blood, having a diameter 2–4 $\mu$m. The identification of platelets as a class of blood corpuscles was described as early as 1882 with the importance of platelets for the formation of a hemostatic plug or clot being first reported about 1888. Another milestone in knowledge about platelets was reached around 1925 when two important concepts in hemostasis (curtailing bleeding or hemorrhaging) were expressed: Aggregations of platelets as they are present in a platelet plug which stops bleeding can only be formed as long as the blood is flowing; and, Formation of fibrin is not a primary event in thrombosis, but is preceded by important changes of the corpuscular elements of the blood. The importance of platelets in the clotting of blood is now well-known.

The number of platelets in a healthy human typically varies from 150,000/mm$^3$ to 300,000/mm$^3$ of blood. While platelets are commonly referred to as cells (and will also be referred to in this disclosure as "cells"), strictly speaking platelets are not cells since they do not have a nucleus. Platelets are produced by the bone marrow, where megakaryocytes (as the results of mitotic proliferation of a committed progenitor cell) liberate platelets as the end product of protrusions of their membrane and cytoplasm. The typical shape of resting platelets is discoid and upon activation they undergo a shape change to a globular form with pseudopodia (up to 5 $\mu$m long) which facilitates the formation of clots.

In modern medical practice, a variety of parameters inform clinicians of the condition of a patient. No surgeon, internist or anaesthetist would treat a patient without assessing liver function, renal function, blood coagulation, blood count and electrolytes before an elective surgical intervention or as follow up in critically ill patients. However, even though a clinician desires an accurate report on blood platelet function, the existing tests do not adequately quantify blood platelet function.

The devices used to quantify blood platelet function are generally referred to as platelet aggregometers. Such platelet aggregometers attempt to evaluate the function of blood platelets and have been in use for many years. Clinical laboratories test for blood platelet function when there is reasonable suspicion that platelet function may be impaired in a patient. Similar tests are also performed on research samples to test the efficacy of various platelet-modifying agents.

Prior methods of assessing platelet aggregation contain inherent flaws related to (1) the testing of the platelets in an unnatural environment (platelets are assessed in an altered sample), (2) the requirement of significant technician time (and associated costs), and (3) the risk of exposing the technician to contact with the blood sample (and the risk of transferring blood-borne pathogens). As explained below, the most common method of assessing platelet aggregation is the optical transmittance method, which requires separating all other blood cells from the platelets. It is conventional wisdom in the industry that separation of platelets from other blood components does not significantly change the behavior of platelets but, as recognized by the present invention, the erythrocytes likely affect the platelet aggregation process and their removal results in an analysis of platelet function in an unnatural environment. Additionally, the procedure for separating the other cells from the platelets is also expected to separate a sub-population of platelets from the sample to be tested, and the removal of that sub-population may further distort the analysis of platelet aggregation. Moreover, the removal of non-platelet cells from the sample requires operator time and exposure of the operator to the risk of contact with any blood-borne pathogens.

One previously available type of existing platelet aggregometer utilizes optical transmittance. Also referred as the turbidometric method, the optical transmittance aggregometers are based on the technique of detection of light transmitted through a cuvette containing platelet-rich plasma (PRP). This technique was originally introduced by Born (Born, G. V. R., Nature, 194: 927–929, 1962) and optical transmittance aggregometers, and variations thereof, are described in U.S. Pat. Nos. 3,989,382 and 4,135,818, 4,066,260 (use of a rotating-disk cuvette), U.S. Pat. No. 5,325,295 (performing the measurement in microwells), U.S. Pat. No. 5,563,041 (adding an inhibitor to more completely prevent fibrin formation), and U.S. Pat. No. 5,569,590 (pre-mixing the needed reagents in a visual-detection system).

As platelets form aggregates, the light transmission through the blood increases in proportion to the aggregation response. The optical transmittance method attempts to detect the shape change, the rate of aggregation, the size of the aggregates, and the maximum aggregation of platelets. However, the recorded responses (except when dose-response techniques are used) can only be qualitative and offer little information relating to the number and size of the platelet aggregates formed. A major limitation of the optical transmission/turbidometric method is that it only works with PRP. Therefore, not only does the optical transmissive/ turbidometric method entail time-consuming processing of blood (centrifugation to obtain PRP), but cells which may be potentially relevant to platelet aggregation (erythrocytes, leukocytes and certain subpopulations of platelets) are removed from the test sample during the centrifugation of the blood sample. All optical transmittance aggregometers disadvantageously require that the blood sample undergo centrifugation to separate leukocytes and red blood cells from the platelets. Centrifugation always results in the loss of some platelets and the previously available devices merely ignore the loss and its effect on quantitative measurements of platelet function. During centrifugation, larger platelets may sediment with the red cells and the effect of their removal on platelet-aggregation tests may well be significant.

Moreover, optical transmittance aggregometers disadvantageously require sample preparation and handling by a trained technician. Moreover, optical transmittance aggregometers disadvantageously assess the platelet function under unnatural conditions, that is in an altered blood sample.

Furthermore, as suggested earlier, preparation of platelet-rich plasma for testing using an optical transmittance aggregometer, as well carrying out the platelet aggregation test, requires manual pipeting and handling of blood by a technician. The manual handling of blood samples is not only time consuming but also exposes the technician to the risk of contact with a blood-borne pathogen. Additionally, red blood cells are known to affect the dynamics of platelet aggregation and with optical transmittance aggregometers using PRP the aggregation is assessed in the absence of red blood cells, thus eliminating possible important variables in the test for abnormal platelet function.

Another device and method for assessing platelet function utilizes the changing electrical impedance of the blood sample. With the electrical impedance method, electrodes are placed in the blood sample to monitor changes in the impedance after a platelet agonist is added to the sample. The electrical impedance method is described in Riess, H., Am. J. Clin. Pathol., 85: 50–56, 1986 and U.S. Pat. No. 4,319,194. The electrode surfaces and electrical effects used in the electrical impedance aggregometer may disadvantageously contribute to the platelet response and aggregation so that the response of the platelets to the aggregating agent alone which is added to the blood sample is not clear when electrical impedance aggregometers are used. In fact, measurements made with electrical impedance aggregometers show no reversal of platelet aggregation under conditions where such reversal is seen in other aggregometers (those using light-transmission measurements in PRP). Disadvantageously, this has led researchers to believe that platelet aggregation in whole blood is irreversible under essentially all conditions, which may not be true.

The electrical impedance method does not require the removal of blood cells from the sample, but dilution of the whole blood sample, generally by 50%, increases measurement sensitivity, which also alters the environment from the natural one in which the platelets normally reside. In addition, the electrical impedance method requires that the platelets adhere to the electrode surfaces immersed in the blood sample.

The impedance method detects the changes in electrical impedance caused by the deposition of activated platelets or platelet aggregates onto two electrodes submerged in the blood sample. The changes in impedance have been shown to correlate positively with platelet aggregation as detected by turbidometric methods. Unlike the turbidometric method, the impedance method allows for the measurement in merely diluted blood. Thus, the impedance method requires less manipulation of the blood sample than the optical transmission method. However, there are several discrepancies between the observations with the impedance method and those with the optical transmission/turbidometric method. When using the impedance method, shape change, disaggregation and biphasic aggregation response are not detectable and platelet response to epinephrine is extremely poor. Moreover, it has been reported that the inhibition of aggregation by antagonists such as aspirin and prostagndin was not normally detected when using the impedance method even though the inhibition of platelet release occurred.

Thus, the impedance method relies upon the adhesion of platelets to the metallic electrodes and is therefore only an indirect measure of platelet aggregation which occurs in the fluid phase. Importantly, the behavior of platelets adhering to an electrode is likely very different than the behavior of platelets adhering to one another in unaltered blood. Furthermore, as with other previously available methods and devices, the blood sample must be transferred to the electrode chamber and then removed again, and the electrodes must be cleaned and reused, both of which require technician time and also exposing the operator to the risk of contact with the blood and any pathogens contained therein.

Yet another method and device which is available for platelet testing is the immobilized platelet stimulant aggregometer. The immobilized platelet stimulant aggregometer measures the adhesion of platelets to an immobilized platelet stimulant. The blood sample or PRP sample is placed in a chamber in which some walls are rotating and some are stationary in order to produce a shear field. The stationary walls are coated with an agent which stimulates platelet adhesion and aggregation, and the rate of platelet response is monitored by a number of means, such as observing the adhesion through the transparent wall or measuring light transmission through the blood (when using PRP). The immobilized platelet stimulant method is described in U.S. Pat. No. 5,523,238 but has not gained widespread acceptance in clinical use.

Yet other lesser used techniques which have been used to measure platelet aggregation include the luminescence method and the platelet counting method. The luminescence method monitors the release of ATP from the dense granule by a firefly luciferin-luciferase assay in whole blood or PRP. In the platelet-counting method, the number of platelets in the test medium is counted intermittently during aggregation. Neither the luminescence method nor the platelet-counting method are considered common laboratory techniques for assessment of platelet aggregation.

In view of the forgoing, it would be an advance in the art to provide a method and apparatus for measuring platelet aggregation which accurately reflects platelet behavior in platelet's normal native environment, including whole blood samples. It would also be an advance in the art to provide an improved method and apparatus to assess platelet aggregation function which utilizes light scattering techniques rather than light transmissive techniques. It would be a further advance in the art to provide a method and apparatus for measuring platelet aggregation which minimizes technician contact with a blood sample being tested and which provides a test which can be carried out quickly and accurately.

BRIEF SUMMARY AND OBJECTS OF THE INVENTION

In view of the above described state of the art, the present invention seeks to realize the following objects and advantages.

It is a primary object of the present invention to provide an improved method and apparatus to assess platelet aggregation and platelet function.

It is another object of the present invention to provide a method and apparatus for measuring platelet function which provides analysis of the platelets using light scattering techniques.

It is also an object of the present invention to provide a method and apparatus for measuring platelet aggregation which accurately reflects platelet behavior in their normal native environment.

It is a further object of the present invention to provide a method and apparatus for measuring platelet aggregation which measures platelet aggregation in a sample of whole blood.

It is yet another object of the present invention to provide a method and apparatus for measuring platelet aggregation which does not require the centrifugation of the blood sample or separation of the platelets from the other blood cells.

It is a further object of the present invention to provide a method and apparatus for measuring platelet aggregation which minimizes technician contact with a blood sample and avoids transfer of blood sample borne pathogens to a technician.

It is also an object of the present invention to provide a method and apparatus for measuring platelet aggregation which can be carried out quickly and accurately.

It is yet another object of the present invention to provide a method and apparatus for measuring platelet aggregation which minimizes the sample preparation which is necessary to carry out a test.

It is yet another object of the present invention to assess platelet aggregation without any need for the technician carrying out the assessment to touch the blood sample.

It is a further object of the present invention to provide a method and apparatus for measuring platelet function which allows disposal of the self-contained test sample after a single use.

It is a still further object of the present invention to provide a method and apparatus for measuring platelet aggregation without the presence of electrical effects and without the requirement of sample dilution.

These and other objects and advantages of the invention will become more fully apparent from the description and claims which follow, or may be learned by the practice of the invention.

The present invention provides a bench-top instrument used to assess platelet function in whole blood. Blood is drawn from patients or research subjects into a sample holder or receptacle containing a standard anticoagulant. The sample holder is then placed in the instrument and the instrument uses light scattering to evaluate the ability of the blood platelets to aggregate in response to standard chemical stimuli.

In some embodiments of the invention, the receptacle is a chamber containing a stirring bar or other stirring device. The diameter of the chamber must be sufficiently large as to provide motion of the platelet aggregates in a circular route. The light from the light source penetrates the blood near the wall of the chamber and the detector responds to scattering events in that blood. The shape of such a receptacle is selected to maximize the velocity of the blood in that region near the wall, since the velocity will be zero at the wall of the receptacle.

It is to be understood that all of the sample holding structures disclosed herein are preferred examples of a means for holding the sample. The sample holding structures disclosed herein are intended to only be exemplary and all structures which perform the same, similar, or equivalent functions which may be presently known in the art or which may become known in the future are all intended to fall within the scope of the means for holding a sample.

In other embodiments of the invention, the receptacle consists of, or includes, a loop of tubing through which the blood is caused to flow. The diameter of the tube is selected so that the light scattering distance does not cause attenuation of signal below that needed for detection and analysis. The desired light-scattering distance has been determined by experience to be less than 2–3 mm, but other distances can be used within the scope of the present invention. Additionally, the diameter of a tube holding the sample should be carefully selected. In some embodiments of the invention, the tube diameter is selected so as to limit the number of platelet aggregates in the scattering volume at the same time. In accordance with the present invention, this diameter is preferably kept smaller than 2–3 mm, but other diameters can be used in accordance with the present invention.

The embodiments of the present invention preferably maintain the blood sample at 37° C. and continuously mix the sample. Once the platelet-aggregating agent is added to the sample, the conditions maintained by the instrument enable platelet aggregation to occur.

It is to be understood that all of the sample holding structures disclosed herein are preferred examples of a means for introducing an aggregating agent into the sample such that platelet aggregation occurs. The syringe and port structures disclosed herein are intended to only be exemplary and all structures which perform the same, similar, or equivalent functions which may be presently known in the art or which may become known in the future are all intended to fall within the scope of the means for introducing an aggregating agent into the sample such that platelet aggregation occurs.

In those embodiments of the invention in which mixing is provided by flowing the sample through a loop of tubing, the velocity through the tubing is controlled in the optimum range. It is to be understood that all of the structures disclosed herein which causes the blood sample to flow, including all types of pumps, are preferred examples of a means for causing flow of the blood through a scattering volume. The pump structures disclosed herein are intended to only be exemplary and all structures which perform the same, similar, or equivalent functions which may be presently known in the art or which may become known in the future are all intended to fall within the scope of the means for causing flow of the blood through a scattering volume.

The light-scattering whole blood aggregometer of the present invention monitors the stimulant induced aggregation of platelets in whole blood by tracking the change in light scattering through the blood sample. The instrument of the present invention mixes the stimulant while focusing light on a scattering volume of the blood sample. A detector positioned at an angle from the incident light senses the intensity of light scattered to the detection position. The detector information is electronically converted to the number and size of platelet aggregates present in the sample at various times after the initiation of the aggregation, which are displayed in a humanly perceptible manner. The present invention also allows for the easy removal and discarding of the blood and the disposable sample compartment.

It is to be understood that all of the source of electromagnetic radiation disclosed herein are preferred examples of a means for illuminating the blood within the scattering volume. The illuminating structures disclosed herein are intended to only be exemplary and all structures which perform the same, similar, or equivalent functions which may be presently known in the art or which may become known in the future are all intended to fall within the scope of the means for illuminating the blood within the scattering volume.

The signal processing components convert the detected light scattering signal into the number and size of the platelet aggregates. This conversion can involve, but is not limited to, the detection of large changes in light intensity compared with a steady or baseline level of intensity when aggregation is not occurring.

It is to be understood that all of the photo detection and many of the signal processing devices disclosed herein are preferred examples of a means for detecting the light scattered by the blood in the scattering volume and generating a scattering signal. The photo detection and signal processing devices disclosed herein are intended to only be exemplary and all structures which perform the same, similar, or equivalent functions which may be presently known in the art or which may become known in the future are all intended to fall within the means for detecting the light scattered by the blood in the scattering volume and generating a scattering signal.

The embodiments of the invention preferably count the number and size of platelet aggregates detected over discrete time intervals, or sequential time periods, and record that information following the addition of the aggregating agent. Those numbers, along with the associated times, are displayed on a selected display device. All of the structures disclosed herein are which provide the user an indication of the number and size of platelet aggregates are preferred examples of a means for processing the scattering signal and displaying at least one platelet aggregation parameter in a humanly perceptible manner. The structures disclosed herein are intended to only be exemplary and all structures which perform the same, similar, or equivalent functions which may be presently known in the art or which may become known in the future are all intended to fall within the scope of the means for processing the scattering signal and displaying at least one platelet aggregation parameter in a humanly perceptible manner.

BRIEF DESCRIPTION OF THE DRAWINGS

In order to better appreciate how the above-recited and other advantages and objects of the invention are obtained, a more particular description of the invention briefly described above will be rendered by reference to a specific embodiment thereof which is illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
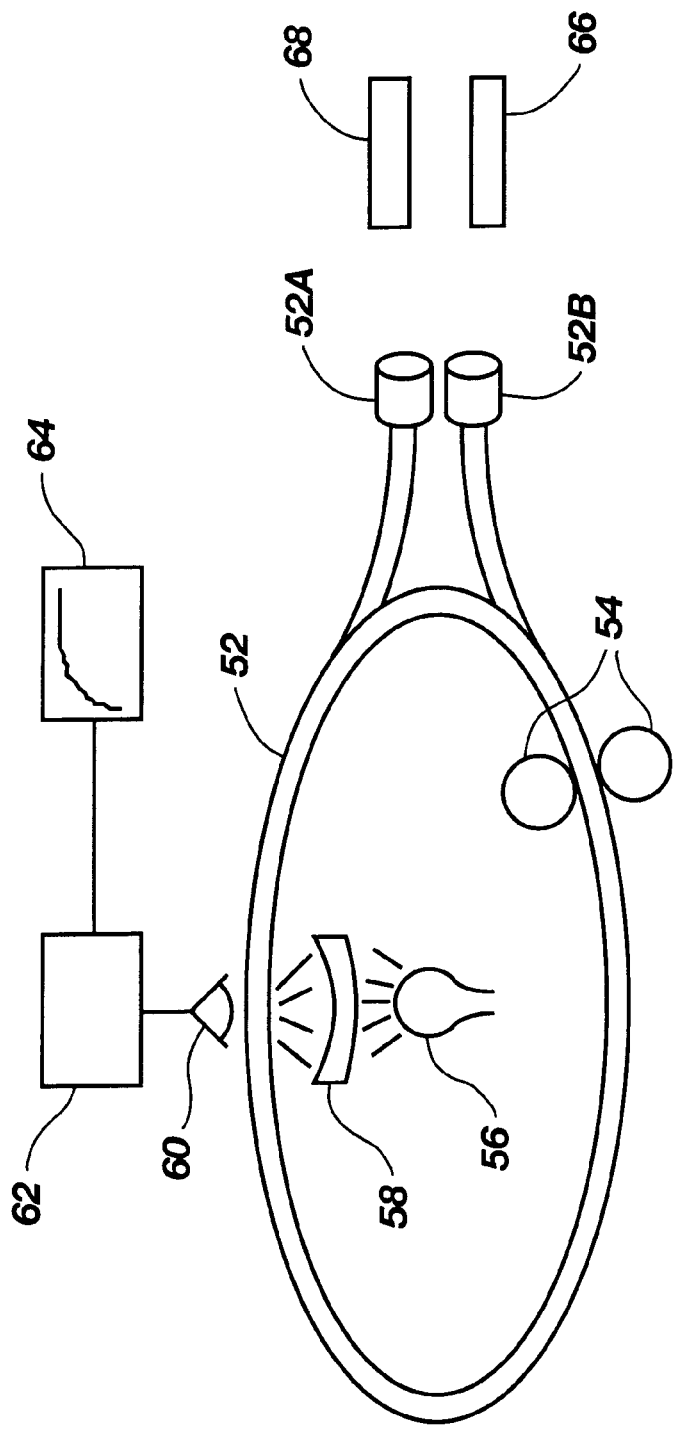
FIG. 1 is a diagrammatic representation of a first presently preferred embodiment of the present invention.

Reference will now be made to the drawings wherein like structures will be provided with like reference designations.

The embodiments of the present invention described herein advantageously use light scattering techniques to assess platelet function. Light scattering techniques provide the present invention with many of the advantages which will be more fully appreciated after consideration of this disclosure, particularly the ability of the present invention to assess platlet function in a sample of whole blood. Light scattering techniques have been used to characterize particulates (determine count and estimate size of) in a number of different applications. However, not until the present invention have the advantages of using light scattering techniques in assessing the function of blood platelets been appreciated and exploited.

Useful information regarding the application of light scattering techniques to the present invention can be gleaned from situations where particles dispersed in a non-scattering medium are assessed. In situations where particles to be counted are dispersed in a non-scattering medium, all scattering events are the result of the particles to be counted and thus is the easiest example of the use of light scattering techniques. In such applications, when no particles are present, no scattering occurs, and when scattering is detected, it can be related directly to the presence of the particles of interest which are to be counted. One known application of light scattering techniques is to "count" the number of cells in bacterial culture. Use of light scattering techniques to count cells in a bacterial culture is described in U.S. Pat. No. 5,293,210.

Importantly, the light scattering techniques used by the present invention most preferably require that platelet aggregations be detected in a whole-blood sample, whole-blood being an optically dense medium. In the case of a whole-blood sample, normal blood cells are present, even without the presence of larger particles (such as large platelet aggregates), and the blood medium causes many scattering events which direct light to virtually all angles from the direction of the incident light. The presence of a large platelet aggregate alters the scattering pattern, so that the intensity of light reaching any location is temporarily changed as that aggregate passes through the scattering volume. It will now be appreciated that obtaining accurate and rapid assessment of platelet aggregation in a whole-blood sample presents challenges not present in the case of detecting particles in a non-scattering medium.

Further useful information on light scattering can also be obtained from applications where the technique is used, along with light absorption techniques, to obtain information about the concentration of certain chemical species in blood as described in U.S. Pat. No. 5,601,080. The '080 patent describes light from one or more sources being directed into a blood sample and the spectral absorption and light scattering signals are measured over a period of time (namely, averaged over time). The obtained signals are used to draw conclusions about the concentrations of certain blood electrolytes, protein, other macromolecules, oxygen, and hemoglobin, as well as about the blood hematocrit and pH. The '080 patent teaches that these parameters are determined assuming that blood is homogeneous in terms of the desired characteristics. This information pertains to the concentrations of molecular species (with the exception of the determination of hematocrit) and does not contain any teaching or suggestion that the number of platelet aggregates (an important assessment to a clinician treating a patient) and the '080 patent clearly does not provide any teaching or suggestion regarding deliberate stimulation of platelet aggregation and then measuring the resultant aggregation. The '080 patent also limits its teachings to average concentrations of certain constituents of blood and is not applied to non-homogeneities such as infrequent cell aggregates. Furthermore, the measurements made in accordance with the teachings of the '080 patent pertain only to the steady condition of the blood sample and do not address changes which may occur in the blood sample over time.

By contrast, the light scattering techniques used in accordance with the present invention preferably provide accurate and frequent measurements made rapidly to determine the content of relatively infrequent platelet aggregates (relatively infrequent in the blood sample when compared with the number of other blood cells such as red and white blood cells and single platelets) after deliberate stimulation of platelet aggregation. Moreover, the techniques of the present invention contemplate assessing rapid changes which take place in a blood sample during the aggregation process and, hence, provide most useful information on the dynamics of a clinically important blood phenomenon, namely platelet aggregation.

Additional information regarding light scattering techniques can also be obtained from applications used to detect embolic material in blood as described in the literature (Transfusion 20: 669–678, 1980 & Biomaterials: Interfacial Phenomena and Applications, Advancement in Chemistry Series No. 199, pp. 59–80, Am. Chem. Sec., Wash. D.C., 1982 & Trans. Am. Soc. Artif. Internal Organs 35: 370–372, 1989 & Am. Soc. Artif. Internal Organs J. 40: M602–608, 1994). In the cases where light scattering techniques are used to detect embolic material, the method involved detecting the embolic material already present in the blood and compiling information about quantity of embolic particles as a measure of blood-material interaction. In addition, the known methods teach using a relatively large volume of blood, typically 20–30 milliliters or a constant source of blood from a live animal. None of the mentioned uses of light scattering techniques teach platelet aggregation which is deliberately induced with pharmacologic agents and further in none of the mentioned instances was the information derived used to assess platelet function per se or to diagnose platelet dysfunction.

When light shines on particles, a fraction of the incoming light is scattered in various directions. The angular distribution of the scattered light intensity depends on the particle size, shape, orientation, position and structure. The scattered light therefore carries information about the characteristics of the particles.

The application of light scattering techniques in accordance with the present invention will now be described. In whole blood, erythrocytes (red blood cells) act as small scatterers (or a scattering medium) of incoming light and produce a large number of multiple scattering events. However, without perturbation by large scatterers (such as platelet aggregates), the scattering pattern of erythrocytes is relatively constant and is recorded as a baseline. When large particles pass through the illuminated volume, the light-scattering pattern is altered briefly and the alterations can be detected, recorded, and analyzed. By monitoring the difference in the scattering pattern as blood flows through the illuminated region, of which the scattering volume as described herein is part, larger particles can be detected in whole blood. Under appropriate conditions, and in accordance with the present invention, the number and magnitude of the alterations in the light-scattering pattern are used to assess the number and size of the large particles passing through the illuminated region, and thus also passing through the scattering volume.

Similarly, in platelet-rich plasma, platelets act as small scatterers of the incoming light. Since these scatterers are dense ($10^8$ per ml) and uniformly distributed in the plasma, the scattering pattern of platelets is similar to that of the red cells in whole blood in that it can be regarded as a constant background. When aggregation occurs, platelets coalesce into larger particles, and the scattering medium of evenly distributed small particles turns into a medium of unevenly distributed large particles. The scattering pattern then becomes one with sporadic large variations (or pulses) as large particles pass through the scattering volume.

In accordance with the present invention, mixing is necessary for platelets to form aggregates while flow of the sample is needed to detect variations in light-scattering. To accomplish the necessary mixing and flow, the test sample (whole blood or PRP) is passed through a scattering volume (an illuminated region) in a fashion which will be described below. The signal which results from the light scattering is received, processed, and displayed to show the number and size of platelet aggregates which form when platelets are challenged by aggregating agents.

The present invention provides advantages not available in the prior art. The preferred embodiments of the present invention provide a self-contained apparatus integrating all components within one housing and providing analysis of a small blood sample (preferably 2 milliliters or less). In accordance with the present invention, platelet aggregation is deliberately induced in the blood sample by the addition of an agonist and an apparatus and method are provided to evaluate the dynamic response of platelets in the sample as a measure of platelet function. Desirably, the embodiments of the present invention do not require the centrifugation of the blood sample or separation of the platelets from the other blood cells. Thus, the time required for sample preparation, necessary in the prior art, is eliminated. Furthermore, the embodiments of the present invention do not require additional handling or processing of the blood sample. Even further, the embodiments of the present invention advantageously provide for analysis of platelet function in the presence of all blood constituents, including red blood cells, thus more accurately reflecting the platelet behavior in their normal native environment.

It will now be appreciated that many of the advantages of the present invention accrue due to detection of the intensity of scattered light rather than to the detection of the intensity of light transmitted through the sample since very little light can be transmitted through whole blood. The apparatus and method of the present invention also provide advantages over available electrical impedance aggregometers because the sample blood is not diluted nor is the sample blood subjected to contact with electrodes or other intensive surfaces which may affect platelet aggregation response.

Presently preferred embodiments of the present invention will now be described. It will be appreciated that the embodiments of the present invention will be referred to as platelet aggregometers and that the embodiments of the present invention all utilize light-scattering phenomenon to assess platelet function in whole blood but it is to be understood that these terms are not intended to be limiting of the scope of the present invention as will be further discussed herein.

Reference will next be made to FIG. 1 which is a diagrammatic representation of a first presently preferred embodiment of the present invention which is generally indicated at 50. The embodiment represented in FIG. 1, and those described herein, is generally referred to as a light-scattering whole blood aggregometer. It is to be appreciated, however, that the use of the term whole blood aggregometer is not intended to limit the scope of the invention claimed herein.

The embodiments of the present invention, including the first embodiment represented in FIG. 1, preferably includes components for carrying out the following functions: (1) Structures for receiving a sample of whole blood; 2) Structures for mixing the blood sample while an aggregating agent is added to the sample and while subsequent platelet aggregation occurs; (3) Structures for illuminating the blood sample with light and for detecting the light scattered from the blood sample; (4) Structures for converting the scattered light signal into information about the extent of actual platelet aggregation in the blood sample; (5) Structures for displaying the platelet aggregation in a humanly perceptible form; and, (6) Structures which allow for disposing of the blood sample and its holding compartment without direct contact of the blood with the operator of the instrument.

Represented in FIG. 1 is a blood sample compartment which consists of a loop of clear flexible tubing 52. During the analysis, the blood to be analyzed, which includes an anticoagulant and preferably amounting to approximately 2–3 ml, is introduced into the tubing 52 directly from a sample syringe 66 into one of two connectors 52A or 52B. The inclusion of a known anticoagulant agent prevents the formation of fibrin clots in the sample. The introduction of the blood from a syringe to the tubing 52 desirably minimizes technician contact with the blood and the accompanying risk of infection by blood borne pathogens. Using a syringe 68, an aggregating agent (well-known in the art) is introduced into the tubing 52, via connectors 52A or 52B or via a needle (not separately represented) through the wall of the tubing 52, to initiate the aggregation of the platelets.

Blood in the tubing 52 is recirculated through the tubing 52 using a roller pump 54. The roller pump 54 is just one example of the structures which are now available or which may become available in the future to cause the sample blood to flow through the container for the sample blood. A control circuit 70 is preferably included to power and control the components represented in FIG. 1, preferably without further intervention from a technician.

A light source 56 produces radiation which is directed through a focusing lens 58 and through the wall of the tubing 52, into the blood contained in the tubing 52, and the intensity of light scattered through the blood and wall of the tubing 52 is detected by a photodetector 60. The area in the sample which is subject to detection is referred to as the scattering volume. The signal produced by the photodetector 60 is processed by a signal processor 62 and the analysis of the platelet function is output on a display 64 in a humanly perceptible manner. The signal processor 62 and the display 64 provide information on the number and size of platelet aggregates present in the sample at various times after the initiation of aggregation. The display 64 can preferably be a video display, a strip chart recorder, or an analog meter, in accordance with the needs of the particular application of the embodiment of the present invention.

The signal processor 62, including any necessary software, firmware, or hardware, converts the signal output from the photodetector 60 into values representing the number and size of the platelet aggregates which pass through the scattering volume. This conversion can involve, but is not limited to, the detection of large changes in light intensity compared with a steady or baseline level of intensity when platelet aggregation is not occurring.

It is preferred that the diameter of the tubing 52 through which the blood flows is selected so that the light scattering distance does not cause attenuation of signal below that needed for detection and analysis. Moreover, the light-scattering distance is preferably less than about 4 mm, more preferably less than about 3 mm, and most preferably less than about 2–3 mm. Additionally, it will be appreciated that the diameter of the tubing 52 should be carefully selected. In some embodiments of the present invention the diameter of the tubing 52 is preferably selected so that only a few, or as few as one, platelet aggregates are present in the scattering volume at the same time. Thus, in accordance with experience gained with the present invention, the diameter of the tubing 52, or other structure through which the blood flows, is preferably less than about 10 mm, more preferably less than about 5 mm, and most preferably less than about 3 mm. It is to be understood that in appropriate circumstances, the diameter and dimensions of the structures carrying out the functions of the present invention can vary from those described herein.

The pump 54 provides both mixing and flow of the sample through the tubing 52. The pump 54, or some other structure to provide flow of the sample, is controlled to provide a flow velocity in an optimum range. Those skilled in the art can select an optimum flow velocity range by contemplating considerations including the fact that the shear rate in the flow should be below the range at which the red blood cells begin to rupture. Velocity ranges for the embodiments of the present invention are preferably such that the shear rates are less than about 2500 s$^{-1}$, more preferably less than about 1500 s$^{-1}$, and most preferably less than about 1000 s$^{-1}$. However, the flow velocity must be sufficient so that the entrance and exit of a platelet aggregate into and out of the scattering volume is sufficiently rapid so as to provide an event which occurs rapidly enough so that the movement of the platelet aggregates into and out of the scattering volume is readily detected. Once the flow velocity is selected, the signal processor 62 can be adapted for optimum performance at the anticipated aggregate flow velocity.

After the platelet aggregate analysis is concluded, the blood which is sealed in the tubing 52, and the tubing 52 itself, are discarded by the technician without risk of contact between the blood and the technician. Advantageously, nothing comes in contact with blood during the measurement process.

Figure 2:
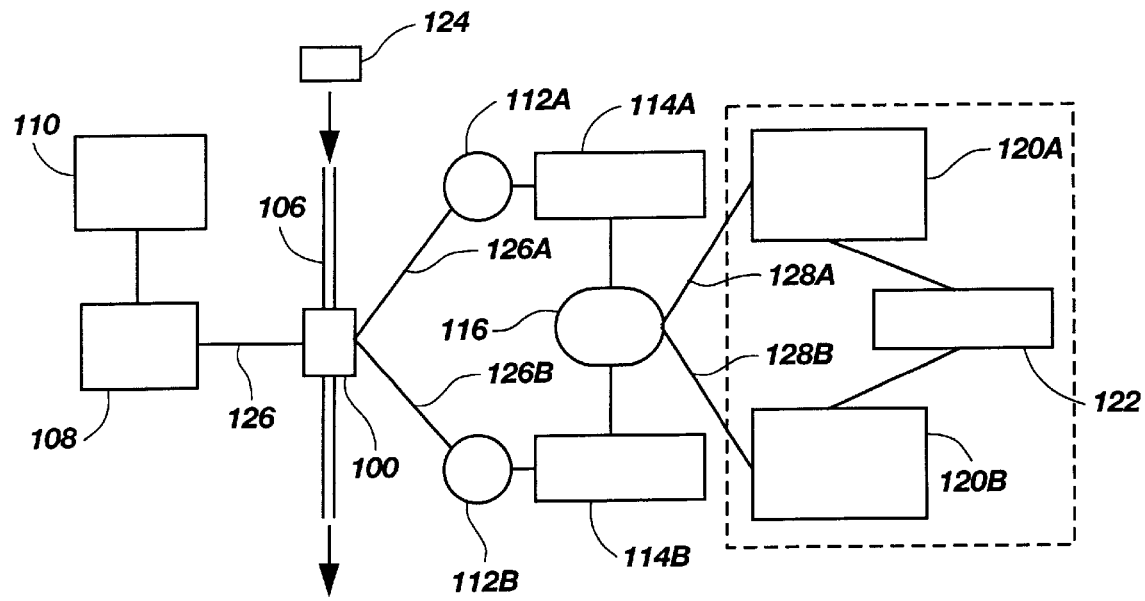
FIG. 2 is a block diagram representing a second presently preferred embodiment of the present invention.

Reference will next be made to FIG. 2 which is a high level block diagram showing the principal functions blocks included in a second presently preferred embodiment of the present invention. The embodiment represented in FIG. 2 is also generally referred to as a light-scattering whole blood aggregometer.

In FIG. 2, flowing blood to be analyzed is represented by arrows 102 and 104 through a tube 106. The tube 106 is preferably clear and sufficiently transparent to allow optical detection there through. It is within the scope of the present invention to utilize any material fashioned into any shape which performs functions which are equivalent to those described herein to hold the blood being analyzed.

A pump 124 is included to provide the necessary mixing and flow of the blood. The blood flow passes through an optic fiber clamp 100. A laser driver 110 drives a laser device 108. The radiation from the laser device 108 is conveyed to the optic fiber clamp 100 via an incident optical fiber 126. The laser light, which preferably is emitted at 830 nm at a power level of 15 mW, is scattered by the blood flowing through the optic fiber clamp 100 and the scattered light is received by the receiving optic fibers 126A&B. It is to be understood that any appropriate wavelengths of light can be used and that the term "light" is intended to mean any appropriate wavelength of electromagnetic radiation and all such wavelengths, including all devices which may now be available or which may be available in the future to generate such radiation, are all intended to fall within the scope of the present invention.

Photodetectors 112A&B receive the output from receiving optic fibers 126A&B, respectively. Amplifiers 114A&B encounter the signals from the photodetectors 112A&B and then the outputs from the amplifiers 114A&B are fed to a conditioning circuit 116. The output from the conditioning circuit 116 is preferably fed to two analog-to-digital converters 120A&B. The output of the analog-to-digital converters 120A&B is fed to an analyzer 122. The analog-to-digital converters 120A&B and analyzer 122 are preferably part of a computer, represented by the box 118, such as an Apple Macintosh compatible computer. It will be appreciated that the hardware represented in FIG. 2 can readily be obtained from sources in the industry or fabricated using the information set forth herein. Similarly, the software functions represented in FIG. 2, particularly the analyzer 122, can be obtained from sources in the industry or can be arrived at by those skilled in the art using the information set forth herein.

Figure 3:
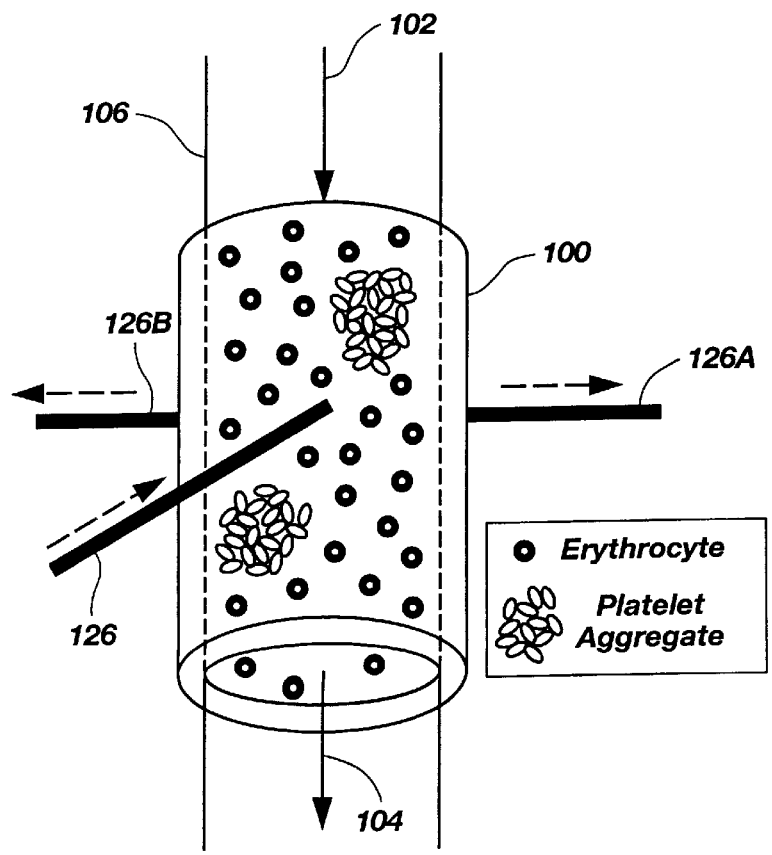
FIG. 3 is a representation of scattering volume in one presently preferred embodiment of the present invention.

Reference will next be made to the detailed view of FIG. 3 to further explain the advantageous use of light scattering techniques in the whole blood aggregometers described herein. As can be seen in FIG. 3, the two receiving optic fibers 126A&B and the incident optical fiber 126 are mounted on the optic fiber clamp 100 so as to direct the ends of each fiber against the wall of the tubing 106. The receiving optic fibers 126A&B and the incident optical fiber 126 are preferably located at the same axial position but at 90° intervals around the circumference of the optic fiber clamp 100 with the incident optical fiber 126 positioned between the two receiving optic fibers 126A&B.

The receiving optic fibers 126A&B and the incident optical fiber 126 are positioned at pre-determined angles from the direction of the incident light in order to detect the intensity of light scattered by the particles of interest. It is to be understood that only one, or more than two, photodetection devices can be used in accordance with the present invention.

The scattering phenomenon important for detecting platelet aggregates represented in FIG. 3 is referred to as Mie scattering (scattering caused by particles which are larger than the wavelength of the light) and information on the characteristics of such scattering can be obtained from van de Hulst, Light Scattering by Small Particles, NY, Wiley, 1957, which is now incorporated herein in its entirety.

Those skilled in the art appreciate that intensity of the scattered light is highly dependent on scattering angle when that angle is small (e.g. less than about 50° to about 60°). Hence, if a detector were placed at a small angle from the incident direction, the variation in the position of a particle would produce changes in the actual angle of scatter associated with light reaching the detector, and the intensity of the light reaching the detector would vary significantly because of that variation in angle. Conversely, the intensity of Mie scattering at angles of 90° or larger is essentially invariant with respect to scattering angle. Thus, the detector, whether a semiconductor optical transducer device or an optical conveyance media leading to an optical transducer device, is preferably positioned at an angle greater than about 45°, more preferably positioned at an angle greater than 70°, and most preferably at an angle greater than about 90° in relation to the direction of incident light. Properly selecting the angle at which scattered light is detected minimizes variations in the detected scattered light intensity due to variations in particle position.

Figure 4:
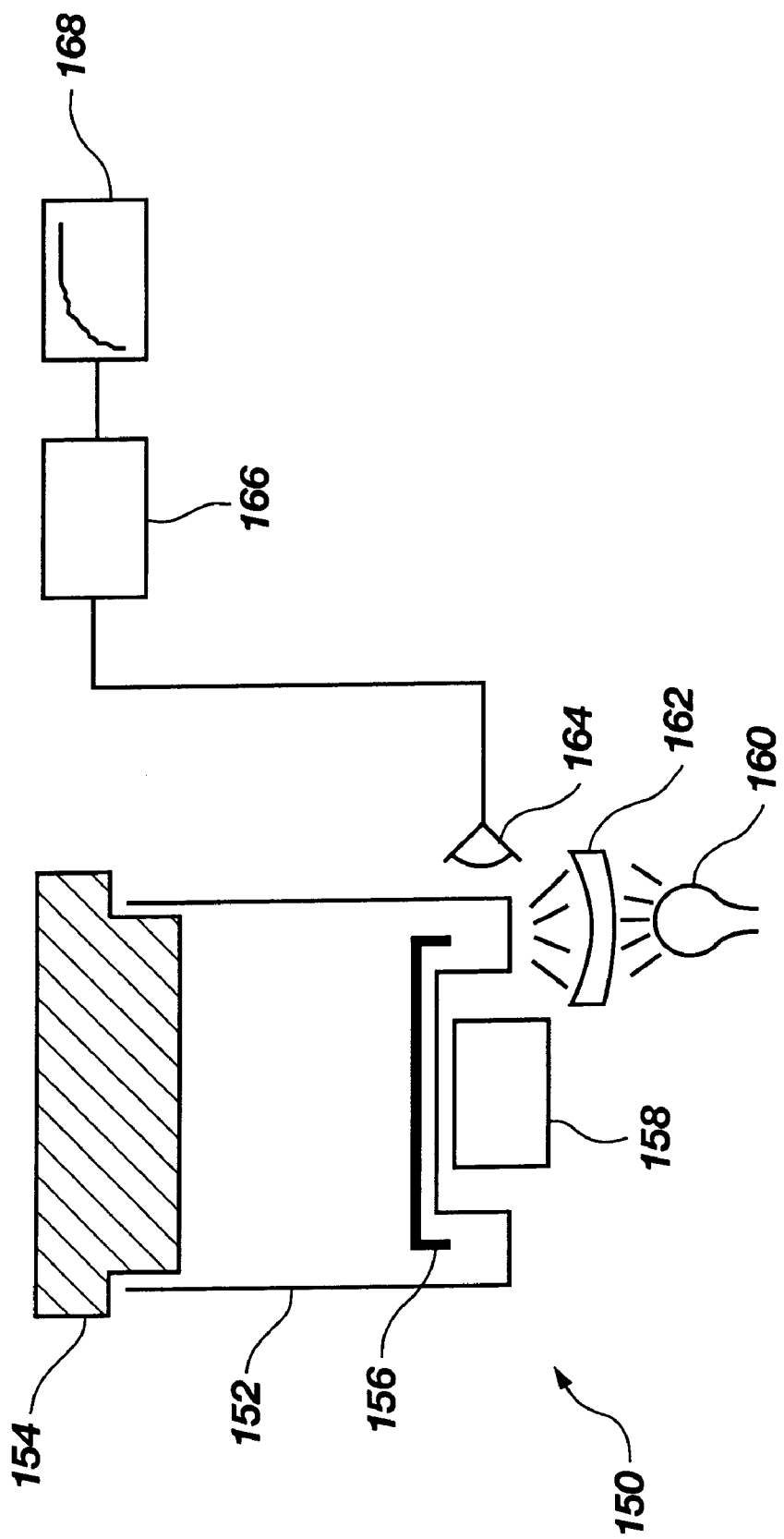
FIG. 4 is a representation of a third presently preferred embodiment of the present invention.

Reference will next be made to FIG. 4 which is a diagrammatic representation of a third presently preferred embodiment of the present invention, generally indicated at 150. The embodiment represented in FIG. 4 is also generally referred to as a light-scattering whole blood aggregometer.

In the embodiment of FIG. 4, the blood container comprises cuvette 152 which is preferably fabricated from a plastic material having the appropriate optical properties. The cuvette 152 preferably has an invaginated center portion as represented in FIG. 4. It will be appreciated that the shape of the cuvette can vary from that illustrated in FIG. 4 and still carry out the same or equivalent functions. A stir bar 156 is positioned within the cuvette 152. The stir bar is activated via a stirring motor 158, for example by a magnetic coupling.

The cuvette 152 is capped with a rubber stopper 154 and has dimensions which allow it to be used with the well-known Vacutainer™ system providing venepuncture. Further, the cuvette 152 is preferably partially evacuated so that the pressure within the cuvette 152 is below atmospheric pressure to draw the correct volume of blood (approximately 2 milliliters). Moreover, it is preferred that the cuvette 152 contains, if desired, the appropriate amount of anticoagulant for that volume of blood. It is also within the scope of the present invention to dispense previously-anticoagulated blood into the cuvette 152 that does not contain anticoagulant and then process such blood with an embodiment of the present invention.

Advantageously, the blood is preferably drawn from the patient directly into the cuvette using the Vacutainer™ system, or some other system available in the art. Collection of blood directly into the cuvette 152, or other sample container, minimizes the risk of technician contact with blood.

An aggregating agent is added to the cuvette 152 containing the sample of blood to initiate the platelet aggregation process. The stir bar 156 circulates the blood sample around the cuvette 152 The light from the light source 160 is directed through the wall of the cuvette 152 into the blood and the intensity of light scattered through the blood and wall of the cuvette 152 is detected by a photodetector 164, in keeping with the considerations described earlier. The output of the photodetector is processed by a signal processor 166 and the results are output in a humanly perceptible form on a display 168 or some other device.

The diameter of the cuvette 152 is preferably sufficiently large as to provide motion of the platelet aggregates in a circular motion. It will be appreciated that many different structures can carry out the function of the stir bar 156 to mix and cause the desired flow of the blood in the cuvette 152. The light from the light source 160 penetrates the outer 1–2 mm of the blood in the cuvette 152 and the photodetector 164 responds to scattering events in that blood. The shape of the cuvette 152, or other structure containing the sample, is preferably selected to maximize the velocity of the blood in that outer 1–2 mm of the cuvette 152 since the flow velocity of the blood will be zero at the wall of the cuvette 152.

At the conclusion of the platelet analysis, the blood and the cuvette 152, containing the blood sample, are discarded by the technician without the risk of contact with blood.

Figure 5:
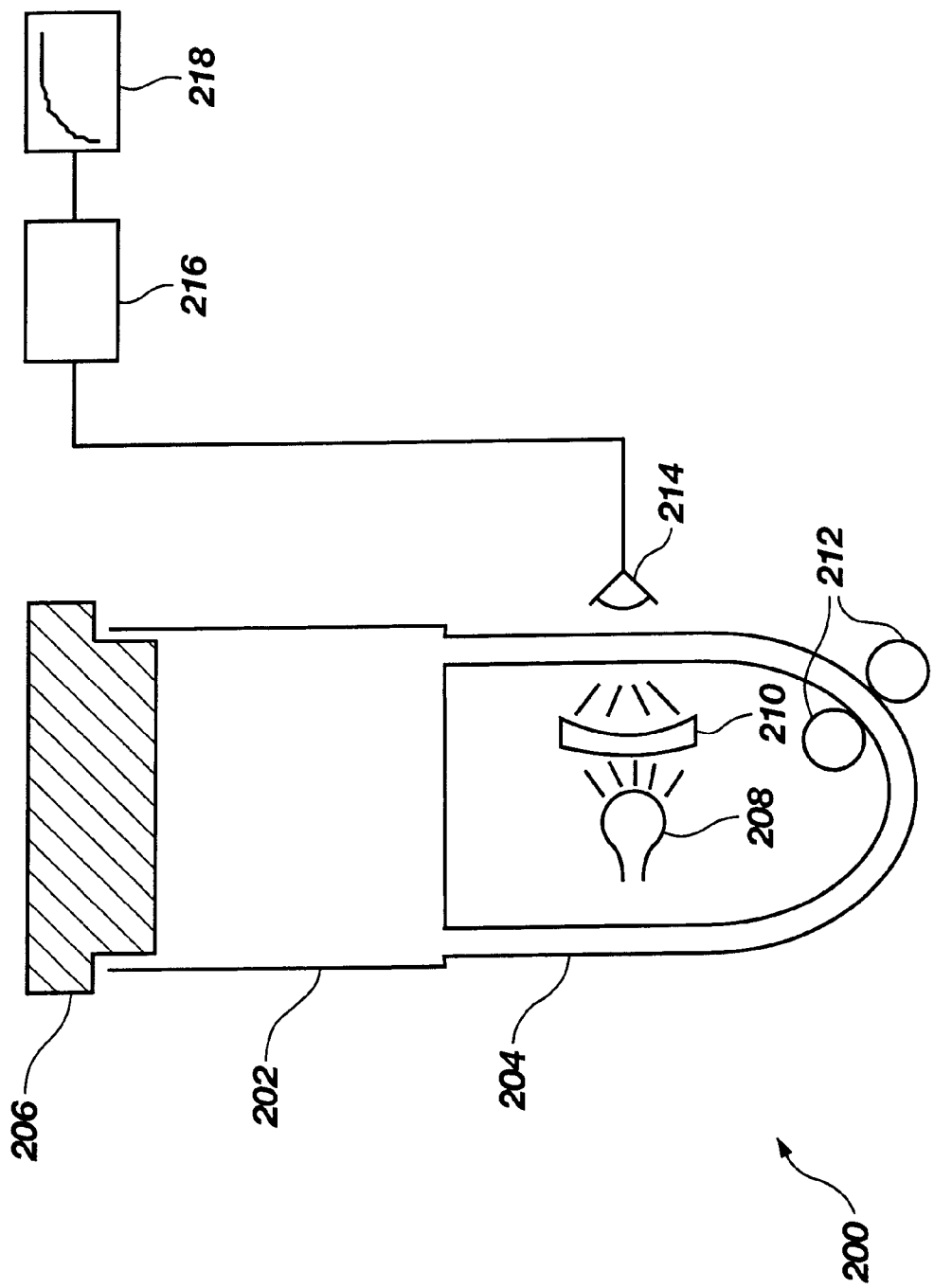
FIG. 5 is a diagrammatic representation of a fourth presently preferred embodiment of the present invention.

Reference will next be made to FIG. 5 which is a diagrammatic representation of a fourth presently preferred embodiment of the present invention, generally indicated at 200. The embodiment represented in FIG. 5 is also generally referred to as a light-scattering whole blood aggregometer.

In the embodiment of FIG. 5, the blood container comprises a cuvette 202 which is preferably fabricated from a plastic material. As will be appreciated shortly, the cuvette 202 can be fabricated without regard to optical properties, except that it is desirable that the contents can be visually observed. Attached to the cuvette 202 is a length of flexible tubing 204 with both ends thereof connected to the cuvette 202 so that any blood sample in the cuvette 202 is communicated to the interior of the tubing 204. The cuvette 202 is capped with a stopper 206. The cuvette 204 and the stopper 206 have dimensions which allow it to be used with the well-known Vacutainer™ system of venepuncture. It is also preferred, as with the previously described cuvettes, that the cuvette 202 is partially evacuated so that the pressure within the cuvette is below atmospheric pressure to draw the correct volume of blood (approximately 2 milliliters) into the cuvette 202. The cuvette 202 also preferably includes an appropriate amount of anticoagulant for the volume of the blood sample. The anticoagulant is preferably present in the cuvette 202 in a form to make it accessible to the blood when it is first drawn, for example being present as a liquid in the cuvette 202 (which provides the advantage of easy mixing) or coated on the surface of the cuvette 202.

Advantageously, the blood is drawn directly into the cuvette 202 using the Vacutainer™ system, as described. The tubing 204 is placed into a roller pump 212. An amount of aggregating agent is added to the cuvette 202 to initiate the platelet aggregation process, for example via a hypodermic needle inserted through the stopper 206. The roller pump 212 circulates the blood sample through the tubing 204 and the cuvette 202. The electromagnetic radiation from a light source 208 is directed through a focusing apparatus 210, through the wall of the tubing 204, and into the blood sample contained in the tubing 204. The intensity of light scattered through the blood and tubing wall is detected by a photodetector 214. The output of the photodetector 214 is processed by the signal processor 216 with an output being preferably shown on a display 218, as discussed earlier. At the conclusion of the analysis, the blood, cuvette 202, and the tubing 204 are discarded by the technician without the risk of contacting the blood sample. It will be appreciated that the considerations discussed in connection with the first, second, and third embodiments are all applicable to the embodiment of the present invention represented in FIG. 5.

Figure 6:
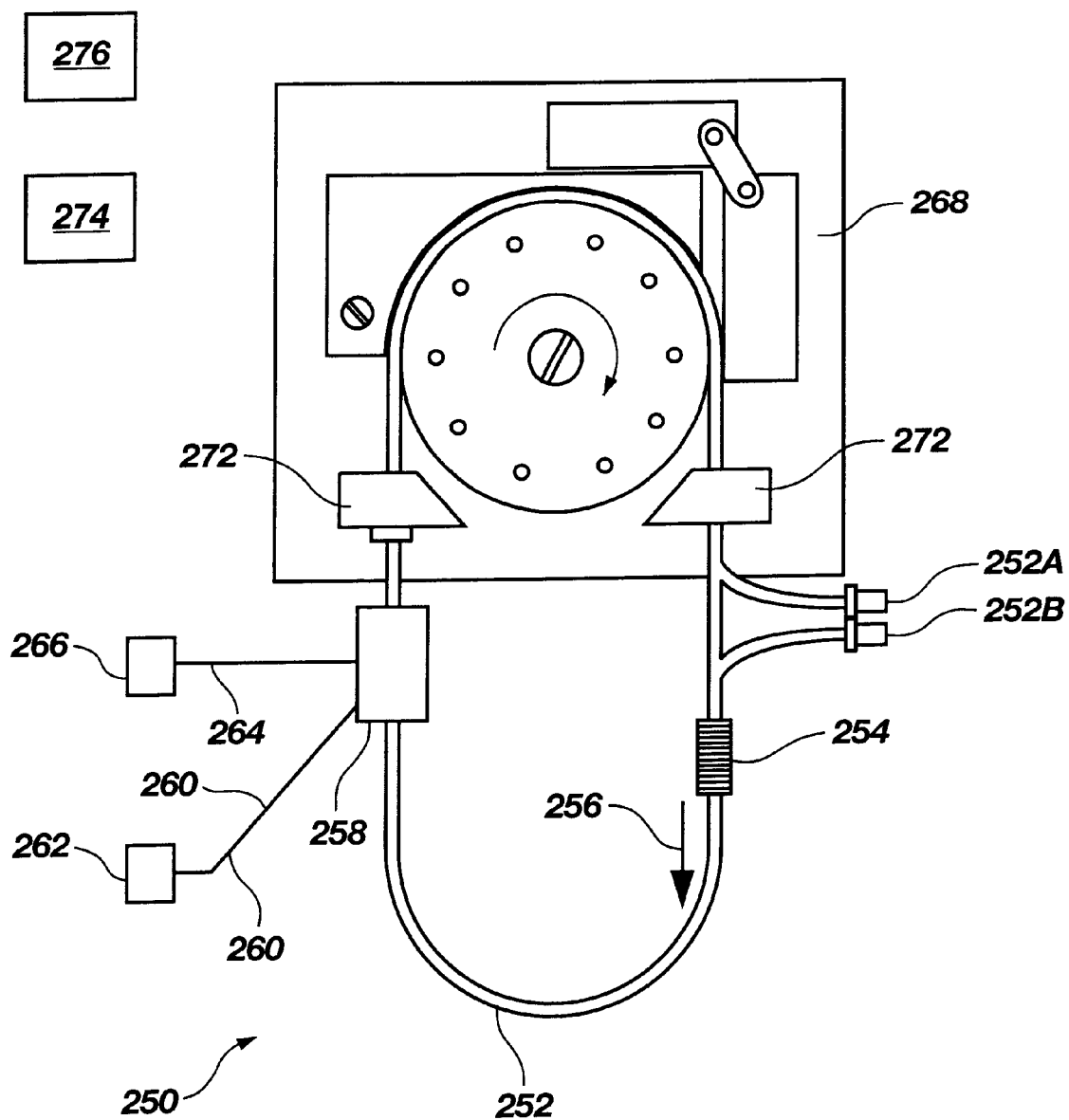
FIG. 6 is a representation of a fifth presently preferred embodiment of the present invention.

Reference will next be made to FIG. 6 which is a diagrammatic representation of a fifth presently preferred embodiment of the present invention, generally indicated at 250. The embodiment represented in FIG. 6 is also generally referred to as a light-scattering whole blood aggregometer.

In FIG. 6 the blood sample is contained in a sample loop 252. The sample loop 252 is preferably fabricated from transparent Tygon™ tubing, 1/16 inch inner diameter, and includes diversion arms upon which connectors 252A&B, which can preferably be the well known luer lock connectors, have been attached. A portion of the tubing 252 is placed in a peristaltic pump 268 and is held in place by clamps 272. The peristaltic pump 268 includes rollers which travel in the direction of arrow 270 to cause flow of the blood sample in the direction of arrow 256. The size of the tubing 252 is preferably such that 2 milliliters of blood (whole blood or PRP) fills the tubing 252 but other sizes and volumes can also be used.

The tubing 252 passes through a fiber optic clamp 258, as discussed in connection with FIG. 2. An incident fiber 260 is connected between a fiber optic clamp 258 and a light source 262. The incident fiber 260 conveys emissions from the light source 262 to the tubing 252 held in the optic fiber clamp 258, as discussed in connection with FIGS. 2 and 3. A receiving fiber 264 is positioned to gather scattered light from the sample and convey it a photodetector 266, as also discussed in connection with FIGS. 2 and 3. A control circuit 274 is preferably provided to control the components of the apparatus 250 and to provide signal processing and display of the analysis results.

Still referring to FIG. 6, examples of the results obtained using the preferred embodiments of the present invention will now be provided. While the examples provided below will be described using the apparatus 250 of FIG. 6, it will be appreciated that the techniques and methods described below have equal applicability with other embodiments of the present invention.

Once a sample is loaded into the tubing 252, as represented in FIG. 6, the pump 268 was activated for at least for one-half minute to equilibrate the temperature at 37° C. It is preferred that the apparatus 250 include a temperature control circuit 276 to maintain the sample at the desired temperature. After thermal equilibrium was reached, a baseline scattering signal was obtained from the photodetector 266. This baseline scattering signal is principally due to erythrocytes and platelets present in the sample.

After a baseline scattering signal was obtained, the pump 268 was switched off and a small volume of aggregating reagent (preferably about 75 $\mu$l) was injected into the sample loop. The pump 268 was switched on and the sample was recirculated at a flow rate of 6 ml per minute.

To obtain a blood sample, human blood was collected by venepuncture of the antecubital vein into a syringe containing 3.8% trisodium citrate (0.38% final concentration). The sample donors denied taking any medication for a minimum of two weeks prior to the blood being drawn. All blood samples were kept at room temperature (23° C.) until testing. In order to provide a comparison to the methods and apparatus of the present invention, platelet-rich plasma samples were prepared by centrifuging anticoagulated blood at 350 g for 10 minutes. PRP was separated from the sedimented red cells and used for turbidometric measurement of platelet aggregation for comparison with the present invention. All aggregation tests were concluded within five hours of blood collection.

The sample loop tubing 252 was filled with about 2 ml of undiluted blood. The optic fiber clamp 258 was placed on the tubing 252 and the control circuit, which is preferably an Apple Macintosh compatible computer, runs a data acquisition program. The data acquisition program can be arrived at by those skilled in the art using the information set forth herein. Preferred functional blocks which may be included in the program are:

Data Acquisition Program
    Initialization Block
        Initialize Variables and Define Functions
        Construct Menus and Event-Handling Routines
        Initialize Acquisition Parameters (sampling rate, sampling time, slot, channels, etc.)
            Construct Text Fields and Buttons
            Insert Default Values
            Wait for Signal from User
            Read Text Fields and Buttons
            Set Acquisition Parameter Values
        Draw Acquisition Graphics
        Calibrate and Set Attenuation Coefficients for Channels 1–8
        Set Selection Thresholds Collection Block
  Display Only Option
    Initiate Data Stream
    Display Data Stream
  Display and Save Option
    Open/Create Data File
    Create Full Pathname from Working Directory
    Save Data Characteristics (sampling rate,
    channels, thresholds, etc.)
    Initiate Data Stream
    Display Data Stream
    Screen Data with Selection Thresholds
    Save Qualifying Data
Data Analysis Program
  Initialization Block
    Initialize Variables and Define Functions
    Construct Menus and Event-Handling Routines
    Initialize Parameters (analysis thresholds)
  File Control Block
    Open Data File or Create Data File (for transfer)
    Read Data Characteristics Parameters
    Read Data
    Reconstruct Time Scale
  Display Block
    Draw Display Graphics
    Display Data
  Analysis Block
    Select Data for Analysis
    Screen Data with Analysis Thresholds
    Compute Data Characteristics (peak frequencies,
    peak heights)
  Output Block
    Choose Output Format
      Display to Screen (histogram, graphical
      summary, statistics)
      Display to Printer (statistics)

An agonist was injected into the tubing 252 and the pump 268 was started and the data acquisition program was initiated to record the development of aggregates in real time. At the end of six minutes the recording was stopped and the data retrieved for analysis. Alternatively, it will be appreciated that the data can be displayed in real time in accordance with the present invention.

The information relating to platelet aggregation was recorded as a series of continuous peaks, the amplitudes of which indicated the sizes of the aggregates. An amplitude was set as a threshold and all peaks above the threshold were regarded as valid aggregates; signals below the threshold were regarded as indistinguishable from the background noise and not counted. The six minutes of recording time were divided into five-second intervals and the amplitudes of the valid peaks within each time interval were averaged to determine the average size of the platelet aggregates. The platelet aggregation profile was the development of the average size and number of the peaks per second with respect to time, along with the product of number and average size to reflect the aggregate volume.

In order to compare the results of the embodiment of FIG. 6 to the prior art, platelet aggregation analysis with the impedance method was also performed following the procedures recommended by the manufacturer of the electrical impedance whole blood aggregometer, Chrono-Log Corp., Ilavertown, Pa.). One ml aliquots of diluted blood (0.5 ml blood plus 0.5 ml saline) were placed in a plastic cuvette and incubated in the aggregometer at 37° C. for three minutes. Agonists were added to the stirred blood, and the change in electrical impedance was recorded by a strip chart recorder. The electrical impedance at the end of six minutes following the addition of the agonist was also recorded by the instrument as the maximal aggregation response.

In order to further compare the results on the embodiment of FIG. 6 to the prior art, platelet aggregation analysis performed with PRP by the optical method using a lumiaggregometer manufactured by Chrono-Log Corp was also carried out. PRP samples were warmed and maintained at 37° C. for 3 minutes. Agonists were then added to the stirred PRP and the aggregation responses recorded for 4 minutes on a strip chart recorder following established procedures.

As mentioned earlier, the effect of platelet aggregation antagonist is important to medical personnel in a clinical setting. Aggregation antagonist prostaglandin $E_1$ ($PGE_1$) was dissolved in ethanol and mixed with autologous platelet-poor plasma (PPP). The PPP containing $PGE_1$ was then mixed with blood or PRP and incubated at 37° C. for 15 minutes. To test the effect of aspirin (acetylsalicylic acid (ASA)) the blood donors were instructed to ingest 1300 mg aspirin during the 12 hours (650 mg at 6 hour intervals) prior to a second blood collection the following day. Appropriate concentrations of agonists were added and the aggregation results before (control) and after the ingestion of aspirin or before and after the addition of $PGE_1$ were compared.

The aggregation and inhibition agents used in these examples were obtained from various sources. Adenosine 5'-diphosphate (ADP) was obtained from Sigma Chemical Co. (St. Louis, Mo.) and dissolved in 0.15 M sodium chloride solution. Collagen was supplied by Chrono-par (Havertown, Pa.) as 1 mg suspended collagen fibrils per ml of isotonic glucose. Ristocetin was supplied by Chrono-par (Havertown, Pa.) and reconstituted with distilled water. Epinephrine was obtained from Sigma (St. Louis, Mo.). Aspirin (acetylsalicylic acid, ASA) was obtained from Bayer Corp. (Elkhart, Ind.). Prostaglandin $E_1$ ($PGE_1$) was obtained from Upjohn Co. (Kalamazoo, Mich.).

The results of these examples will be discussed below.

Figure 7A:
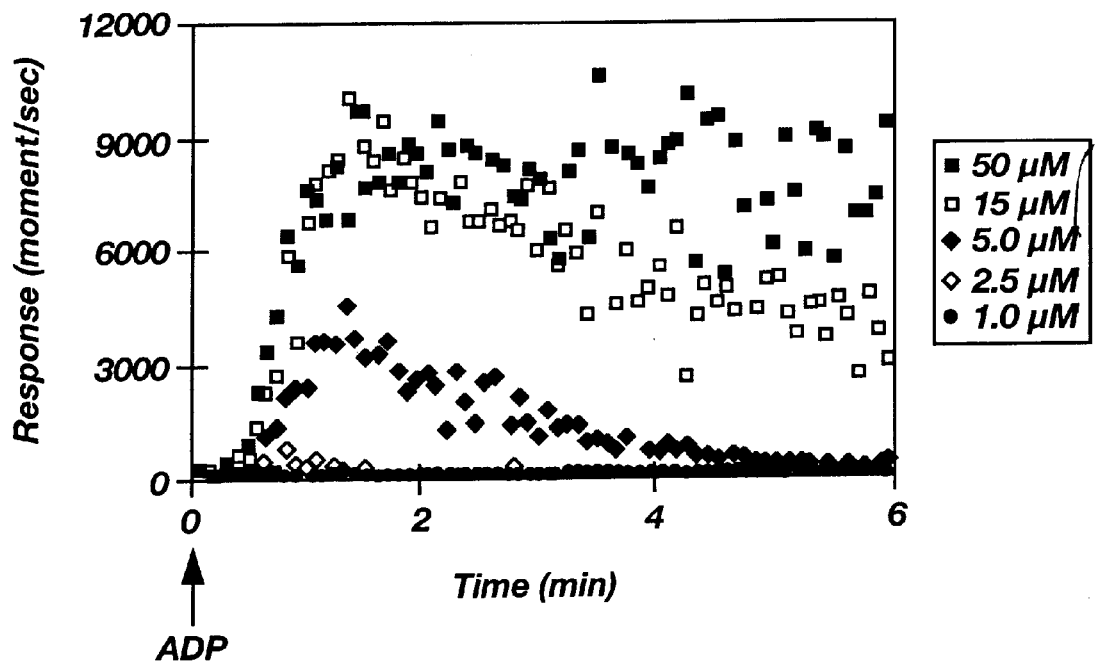
FIGS. 7A, 8A, 9A & 10A and 7B, 8B, 9B & 10B are graphs comparing the results obtained using the apparatus represented in FIG. 6 to the results obtained using a previously available electrical impedance aggregometer, respectively.
Figure 7B:
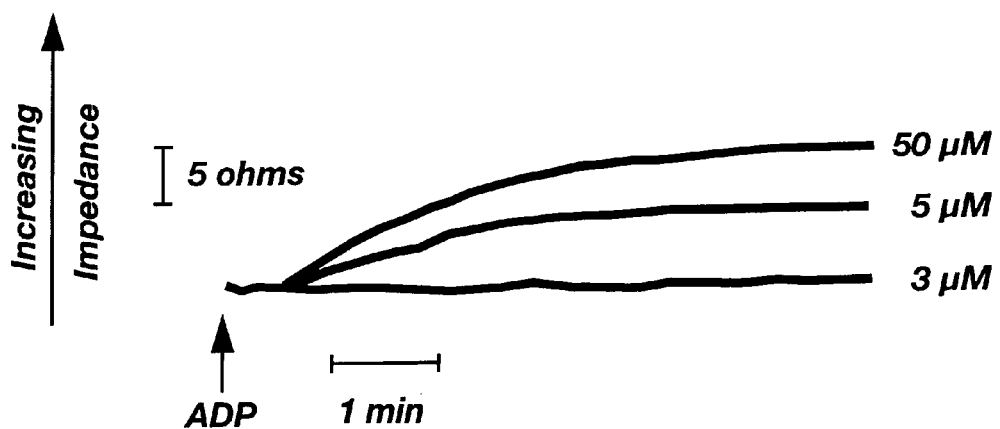

Platelet aggregation responses induced by collagen, ADP and ristocetin were readily detected by the apparatus 250 of FIG. 6 and a dose-dependent platelet aggregation response by ADP was established (FIG. 7A). At low concentrations of ADP (<5 $\mu$M), the platelet aggregations were often reversible while at higher concentrations of ADP, they were irreversible.

Figure 8A:
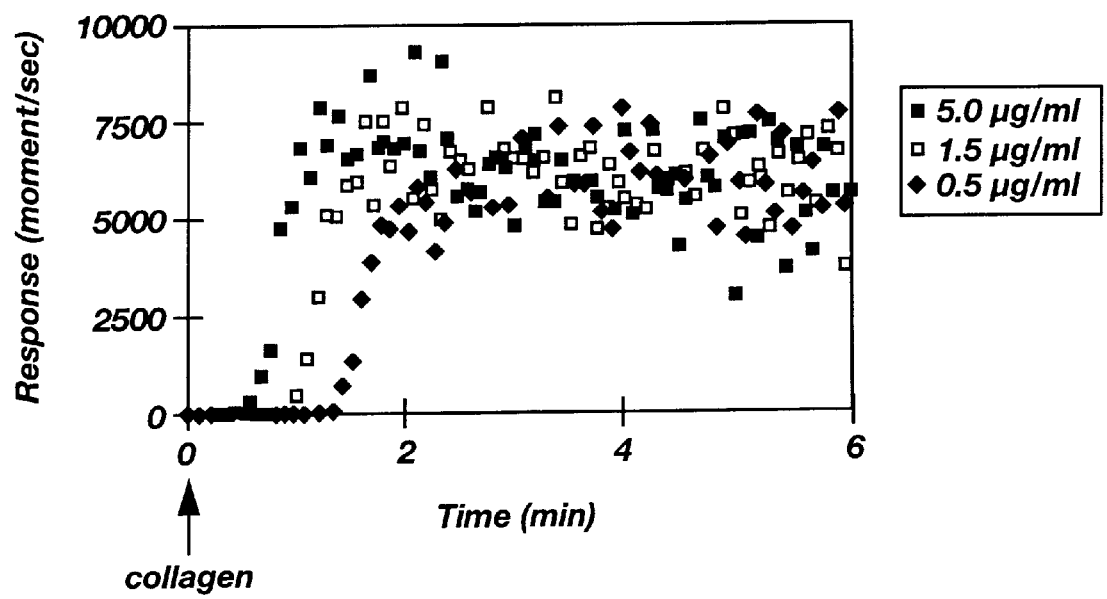
Figure 8B:
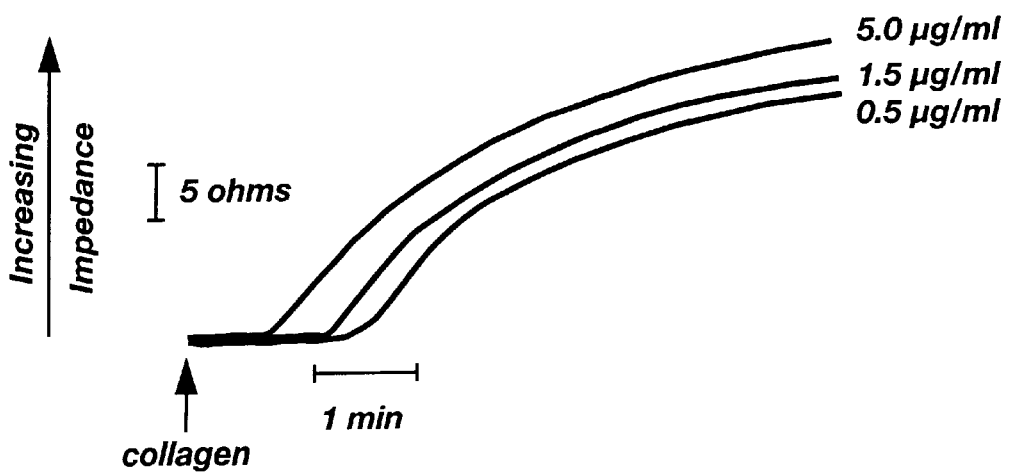

A dose-dependent platelet aggregation response by collagen was noted with the apparatus 250 of FIG. 6 (response shown in FIG. 8A). While higher concentrations of collagen produced more rapid onset of aggregation, all concentrations of collagen produced the same maximal aggregation although with different slopes (FIG. 8A).

In four out of six human subjects, epinephrine failed to induce platelet aggregation in whole blood even at 100 $\mu$M. However, platelets aggregated when challenged by 10 $\mu$M epinephrine in the two other donors.

Figure 9A:
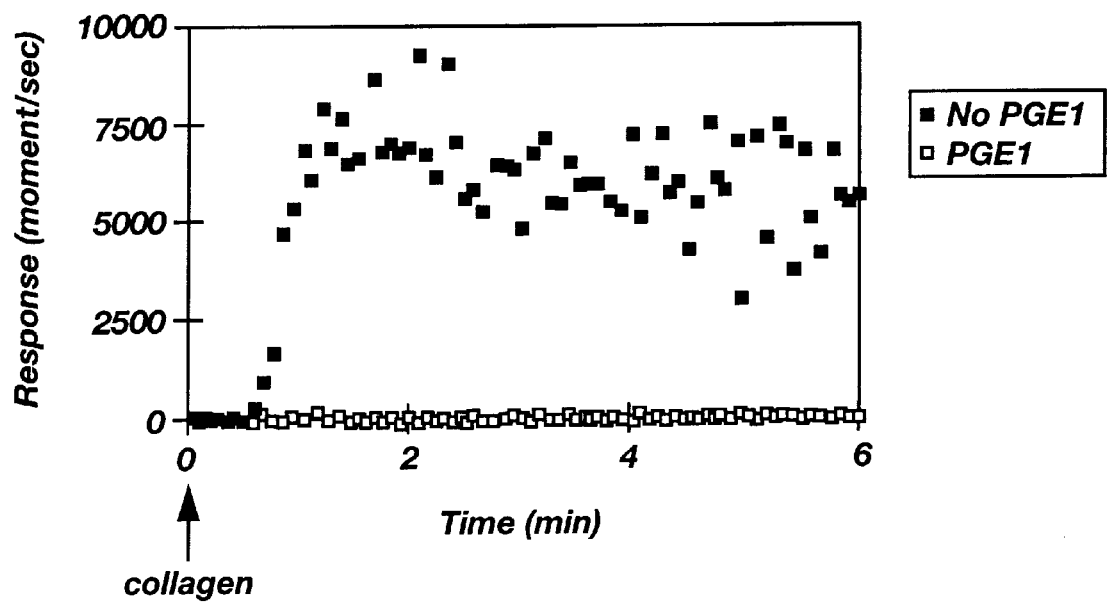
Figure 9B:
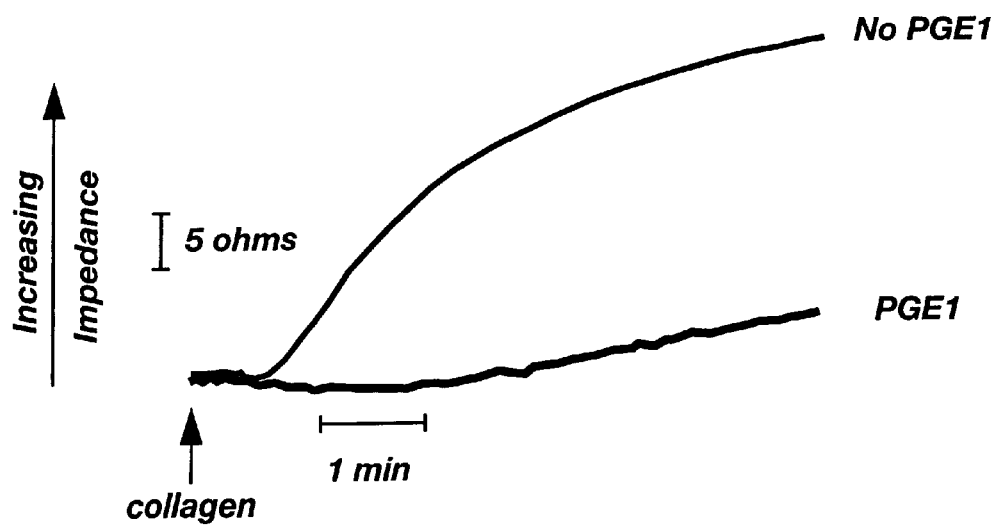
Figure 10A:
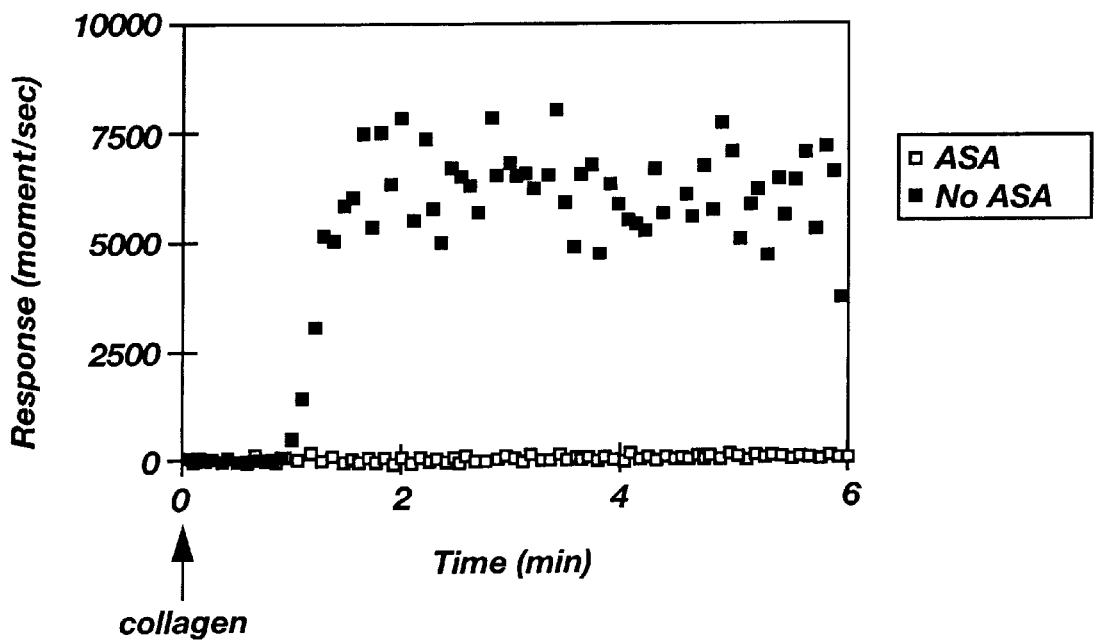
Figure 10B:
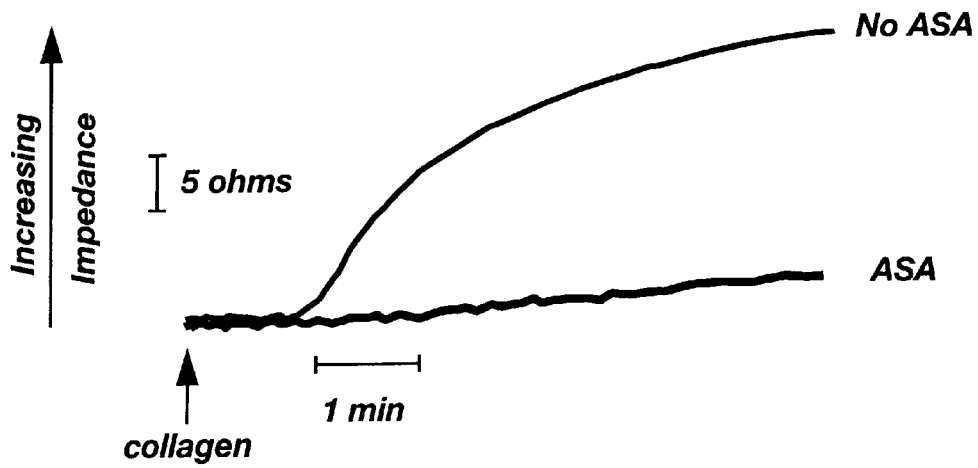

The light-scattering aggregometer represented in FIG. 6 was capable of detecting the inhibition of aggregation. Incubation of blood with 10 $\mu$M PGE, completely inhibited collagen-induced aggregation (FIG. 9A). Blood drawn from human subjects after the ingestion of aspirin showed significant inhibition of aggregation when 1.5 $\mu$g/ml collagen was added (FIG. 10A). However, at 5 $\mu$g/ml collagen, the inhibition was less pronounced (data not shown in the figures).

A comparison of the results obtained using the embodiment of the present invention represented in FIG. 6 and the results obtain using the previously available devices shows the advantages of the present invention.

An electrical impedance whole blood aggregometer was used to measure platelet aggregation and inhibition in blood. As shown by the strip chart recorder tracings provided in FIGS. 7B, 8B, 9B, and 10B, the results obtained using the apparatus 250 of the present invention were as good or better than the results obtained using an electrical impedance whole blood aggregometer. Importantly, FIGS. 7A&B, 8A&B, 9A&B, and 10A&B show that better results are obtained using the apparatus 250 of the present invention in two particular areas: (1) The reversal of aggregation at low doses of ADP could not be detected with the electrical impedance whole blood aggregometer; and, (2) The blood donors whose platelet aggregation at 10 $\mu$M epinephrine was observed with the apparatus 250 of the present invention but showed no epinephrine-induced aggregation response with the electrical impedance whole blood aggregometer.

Figure 11A:
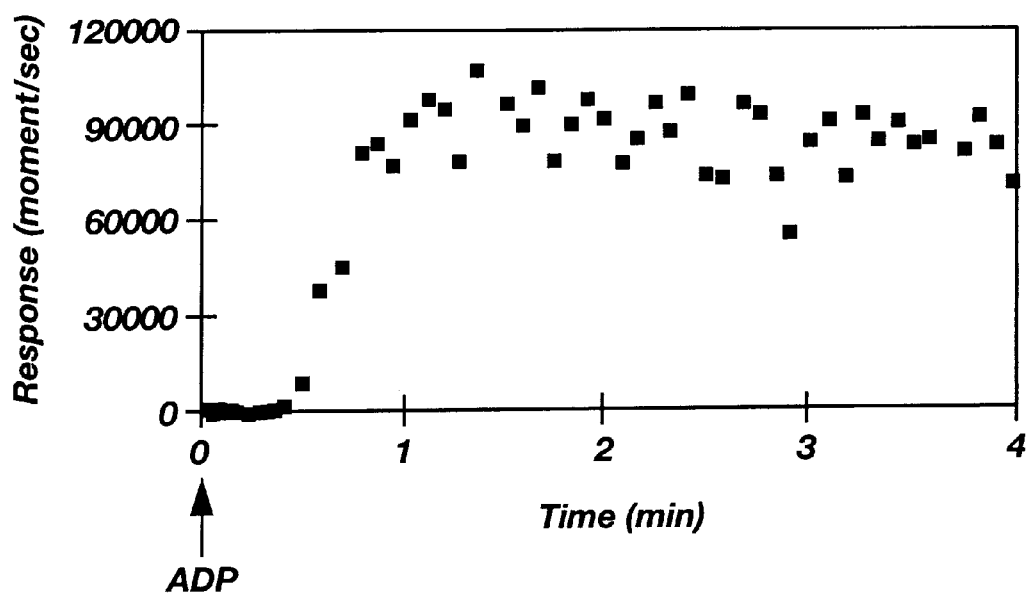
FIGS. 11A & 12A and 11B & 12B are graphs comparing the results obtained using the apparatus represented in FIG. 6 to the results obtained using a previously available optical transmittance aggregometer, respectively.
Figure 11B:
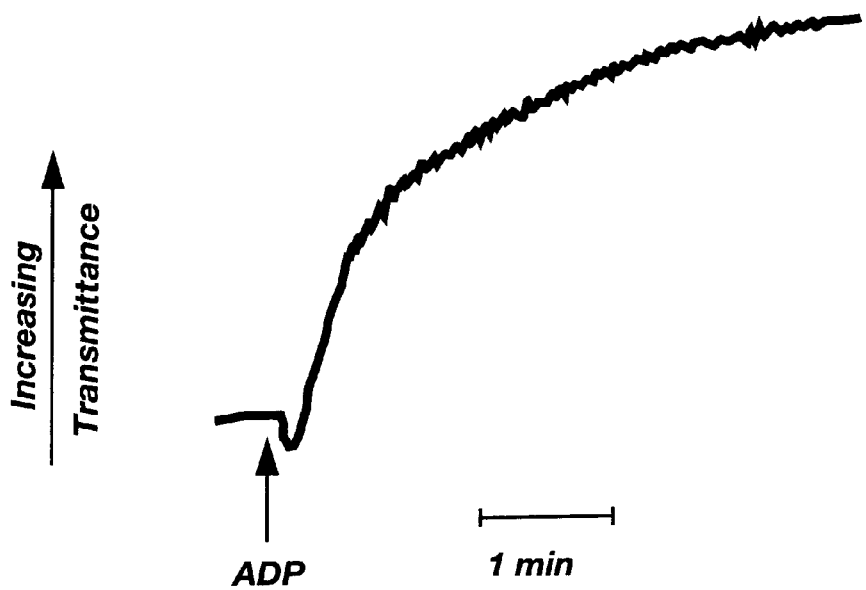
Figure 12A:
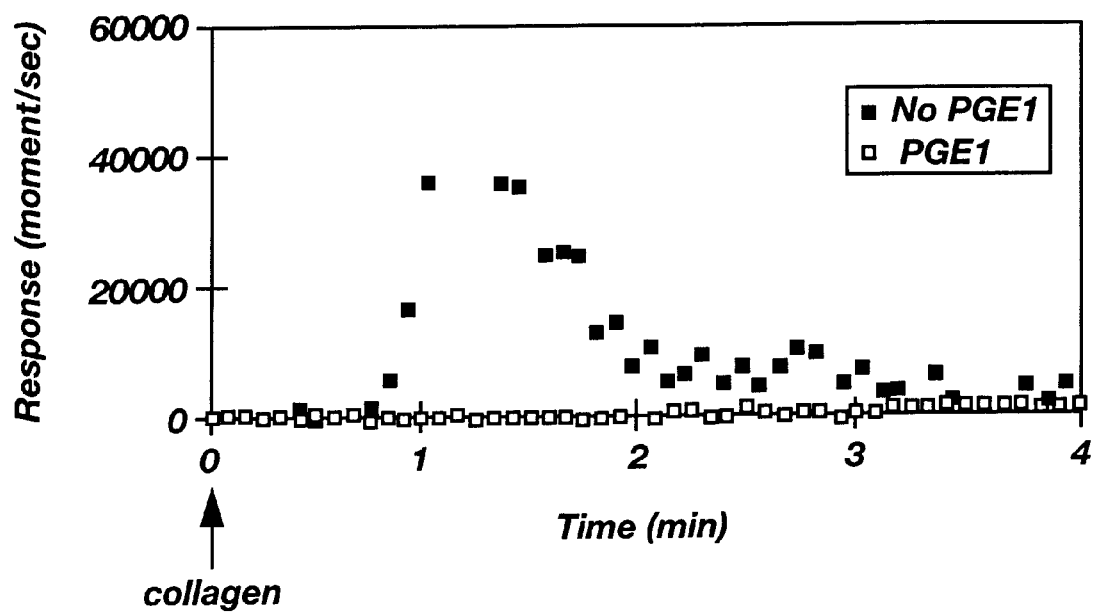
Figure 12B:
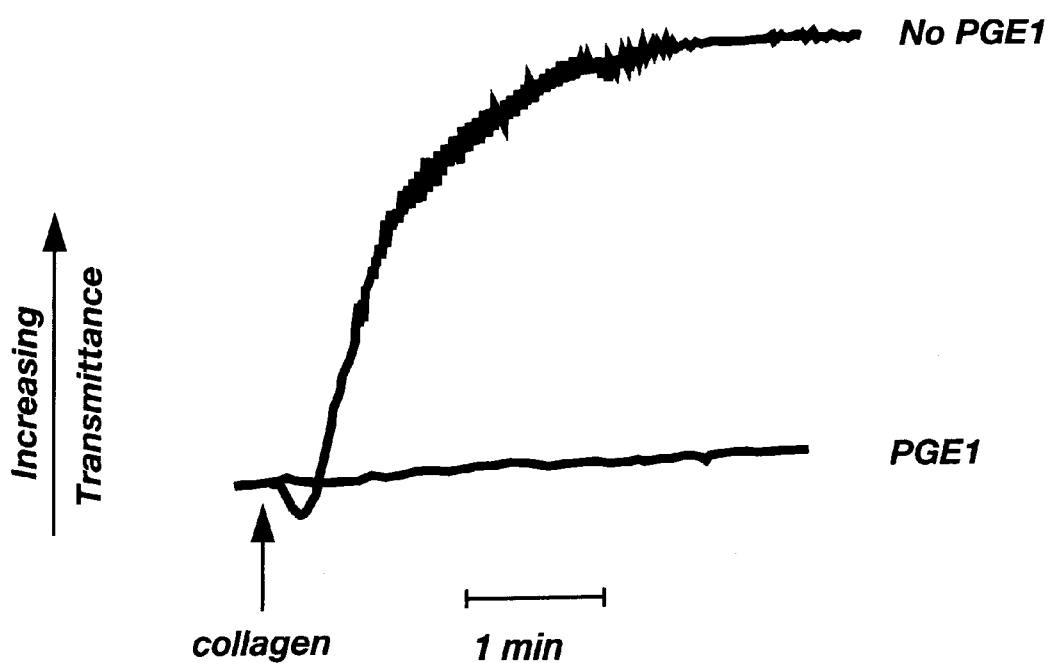

Platelet aggregations in PRP were also conducted with the apparatus 250 of the present invention represented in FIG. 6 and the results compared with those obtained with an optical aggregometer. Aggregation responses induced by collagen, ADP, ristocetin and epinephrine, and inhibition of aggregation by PGE, were all detected with the apparatus 250 of the present invention and with the optical aggregometer. The results of the analysis conducted using the apparatus 250 of the present invention is represented in FIGS. 11A and 12A. The results of the analysis conducted on the same samples using an available optical aggregometer is represented in FIGS. 11B and 12B. As can be seen from FIGS. 11A and 12A, large platelet aggregates formed in the tubing (252 in FIG. 6) which formed the sample loop. These large platelet aggregates recruited a significant number of platelets and often stuck to the tubing wall (confirmed by visual inspection of the tubing after the end of the procedure), causing diminished light-scattering signal to be detected as seen in FIG. 12A. The noted loss of light-scattering signal was relatively rapid and distinguishable from the loss of light scattering signal during disaggregation of platelets, which occurred gradually over a period of minutes, as shown by FIG. 11A.

In view of the forgoing, it will be appreciated that the present invention provides improved assessment of platelet function. The present invention provides significant advantages over the available optical aggregometers which work only with PRP. Disadvantageously, the prior art requirement of using PRP raises several questions: (1) The centrifugation of blood to prepare PRP may subject platelets to stress and alter their properties; (2) Preparation of PRP takes approximately 30 minutes, and labile aggregation modulators such as thromboxane, $A_2$, and prostacyclin may decay substantially during sample preparation thus degrading the resulting assessment; and, (3) Erythrocytes, leukocytes, and certain subpopulations of platelets are discarded during PRP preparation and the influence of these blood components on platelet aggregation is ignored by prior art optical aggregometers.

Furthermore, the electrical impedance prior art method eliminates the need to use PRP, but to obtain optimal results the blood sample must be diluted with saline, which dilutes the blood and is expected to effect the aggregation response of platelets. The electrical impedance method is essentially based on a measurement of thrombus growth on the electrodes which reflects adhesion of platelets whereas platelet aggregation occurs in the fluid phase. The adhesion of platelets to the electrodes and the fact that aggregation reversal cannot be detected in blood with the impedance method indicate that this technique measures the cumulative effect of platelet aggregation and adhesion rather than the instantaneous effect of platelet aggregation, as is measured by the present invention. Therefore the impedance method may not be adequate in providing information concerning the dynamics of platelet aggregation in blood, particularly the rapidity with which aggregates form as well as the number and size of these aggregates at any time during the aggregation process.

Advantageously, the apparatus and method of the present invention can follow the onset and progression of platelet aggregation in real time. The apparatus and method of the present invention not only provides qualitative information on aggregation, as measured by available methods discussed above, but the apparatus and method of the present invention also provides quantitative information regarding the number and size of aggregates at any given time during the analysis.

Reference will next be made to the ordinate of the graphs in FIGS. 7A to 12A, where moment is the product of the number of peaks multiplied by the height of the peaks. of great advantage is that the apparatus and method of the present invention allows the light-scattering measurement to be made in undiluted blood since it allows platelet aggregation to occur in blood with all its components at their physiological concentrations.

The comparative data presented in FIGS. 7A&B compared to 12A&B shows that: (1) The results obtained from the previously available impedance or light-scattering aggregometers were generally similar; (2) The establishment of dose-responses using ADP and collagen with the apparatus of the present is capable of differentiating and quantifying aggregation response which is not possible with all prior art methods; (3) The method and apparatus of the present invention allows measurement of the inhibition of aggregation following the addition or ingestion of platelet inhibitors which is not possible with all prior art methods; and, (4) Platelet aggregation in PRP was detectable with the present invention. These observations confirm that the apparatus and method of the presented invention is a valid technique to assess platelet aggregation.

The absence of epinephrine-induced aggregation (with 100 $\mu$M epinephrine) in most donors observed with the method and apparatus of the present invention corroborated earlier similar findings involving the impedance method. Since human erythrocytes have adrenergic receptors and are known to bind epinephrine, the lack of epinephrine-induced aggregation in blood may be in part due to erythrocytes competing with platelets for the available epinephrine, Epinephrine-induced platelet aggregation is not a problem in PRP where competing erythrocytes are not present. It is not clear why two human subjects responded to epinephrine in blood whereas the other four failed to exhibit the same response. As for the fact that the impedance method failed to demonstrate epinephrine-induced aggregation in the two donors, with whom a response was noted with the present invention, indicates that the present invention is more sensitive than the impedance method in detecting subtle changes in platelet function.

The present invention advantageously utilizes light-scattering in a whole blood aggregometer which detects platelet aggregation in undiluted blood. Among the principal features of the present invention are: (1) Only a small volume of undiluted blood is needed to conduct the test; (2) The present invention is more sensitive than the electrical impedance aggregometer in detecting changes in platelet function; (3) The present invention measures the number and size of platelet aggregates in real time, a feature which is not possible with existing platelet aggregometers; and (4) Aggregation experiments can be performed in a closed loop and eliminates the need for a technician to be exposed to blood being tested.

In view of the forgoing it will be appreciated that the present invention provides an improved method and apparatus to assess platelet aggregation function which utilizes light scattering techniques. The present invention also provides a method and apparatus for measuring platelet aggregation which accurately reflects platelet behavior in their normal native environment, including unaltered whole blood samples. Moreover, the present invention also provides a method and apparatus for measuring platelet aggregation which avoids human contact with a blood sample being tested and which provides a test which can be carried out quickly and accurately.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for assessing the function of platelets in a sample of whole blood, the apparatus comprising:
    means for holding the sample, wherein the sample comprises whole blood;
    means for causing flow of the whole blood through a scattering volume;
    means for introducing an aggregating agent into the sample of whole blood such that platelet aggregation occurs;
    means for illuminating the whole blood within the scattering volume;
    means for detecting the light scattered by the whole blood in the scattering volume and generating a scattering signal; and
    means for processing the scattering signal and displaying at least one platelet aggregation parameter in a humanly perceptible manner whereby the volume of the means for holding the sample is such that the light scattered is not attenuated below that needed for detection and analysis of platelet aggregation within the sample.

2. An apparatus as defined in claim 1 wherein the means for holding comprises a container having a volume in the range from about 1 ml to about 5 ml.

3. An apparatus as defined in claim 1 wherein the means for holding comprises a cuvette, the cuvette comprising:
    an optically clear portion adjacent to the scattering volume; and
    a channel formed in the cuvette, the channel including the optically clear portion.

4. An apparatus as defined in claim 1 wherein the means for holding comprises:
    reservoir for holding the sample of blood;
    an inlet on the reservoir;
    an outlet on the reservoir;
    a conduit having a first end and a second end, the first end being connected to the inlet and the second end being connected to the outlet such that at least a portion of the sample of blood can flow through the conduit.

5. An apparatus as defined in claim 4 wherein the conduit comprises a substantially optically clear flexible tube having a diameter less than about 3 mm.

6. An apparatus as defined in claim 4 wherein the reservoir includes an interior and further comprising an anticoagulant contained within the conduit before receiving the sample.

7. An apparatus as defined in claim 4 wherein further comprising an anticoagulant fixed to the interior of the reservoir.

8. An apparatus as defined in claim 1 wherein the means for holding comprises a length of tubing.

9. An apparatus as defined in claim 1 wherein the means for causing flow of the blood comprises a pump.

10. An apparatus as defined in claim 9 wherein the pump comprises a peristaltic pump.

11. An apparatus as defined in claim 1 wherein the means for introducing comprises a penetrable member on the means for holding.

12. An apparatus as defined in claim 1 wherein the means for introducing comprises a hypodermic needle and a syringe containing the aggregating agent.

13. An apparatus as defined in claim 1 wherein the means for introducing comprises an agonist injection port provided on the means for holding the sample.

14. An apparatus as defined in claim 1 wherein the means for illuminating comprises an electromagnetic radiation source.

15. An apparatus as defined in claim 1 wherein the means for illuminating comprises a laser.

16. An apparatus as defined in claim 15 wherein the laser comprises a semiconductor laser emitting radiation at about 830 nm.

17. An apparatus as defined in claim 1 wherein the means for illuminating comprises:
    a coherent light source;
    an optical fiber connected to the coherent light source so that light is emitted from an end of the optical fiber; and
    means for aiming the light emitted from the end of the optical fiber into the scattering volume.

18. An apparatus as defined in claim 1 wherein the means for detecting comprises a photodetector.

19. An apparatus as defined in claim 1 wherein the means for detecting comprises at least a first photodetector and a second photodetector, the first and second photodetectors being positioned about the scattering volume opposite each other.

20. An apparatus as defined in claim 1 wherein the means for detecting and the means for illuminating are oriented at an angle greater than 70° about the scattering volume with respect to each other.

21. An apparatus as defined in claim 1 wherein the means for detecting and the means for illuminating are oriented at an angle of about 90° about the scattering volume with respect to each other.

22. An apparatus as defined in claim 1 wherein the means for detecting and the means for illuminating are oriented at an angle around the scattering volume with respect to each other such that the light scattered by platelet aggregates in the sample of blood tends to be maximized.

23. An apparatus as defined in claim 1 wherein the means for detecting and the means for illuminating are oriented at an angle of about 90° around the scattering volume with respect to each other such that the light scattered by platelet aggregates in the sample of blood tends to be maximized.

24. An apparatus as defined in claim 1 wherein the means for processing comprises a microprocessor.

25. An apparatus as defined in claim 1 wherein the platelet aggregation parameter comprises the parameters selected from the group consisting of:

the number of platelet aggregates formed; and the size of the platelet aggregates formed.

26. An apparatus as defined in claim 1 wherein the means for processing the scattering signal and displaying at least one platelet aggregation parameter in a humanly perceptible manner comprises a visual display, the visual display selected from the group consisting of: a video display, a strip chart recorder, and an analog meter.

27. A method for assessing the function of platelets in a sample of whole blood, the method comprising the steps of:

collecting a sample, wherein the sample comprises whole blood;

causing the sample of whole blood to flow through a scattering volume;

introducing an aggregating agent into the sample of whole blood such that platelet aggregation occurs;

illuminating the sample of whole blood within the scattering volume;

detecting the light scattered by the whole blood in the scattering volume and generating a scattering signal; and processing the scattering signal and displaying at least one platelet aggregation parameter in a humanly perceptible manner whereby the volume of the scattering volume is such that the light scattered is not attenuated below that needed for detection and analysis of platelet aggregation within the sample.

28. A method as defined in claim 27 wherein the step of collecting a sample comprises the step of collecting a sample having a volume of about 2 ml.

29. A method as defined in claim 27 wherein the step of collecting a sample comprises collecting a sample of whole blood without removal of any blood constituents.

30. A method as defined in claim 27 wherein the step of collecting comprises the step of collecting the blood in a cuvette, the cuvette comprising:

an optically clear portion adjacent to the scattering volume; and a channel formed in the cuvette, the channel including the optically clear portion.

31. A method as defined in claim 27 wherein the step of collecting a sample comprises the step of collecting a sample in a means for holding blood, the means for holding comprising:

a reservoir for holding the sample of blood;

an inlet on the reservoir;

an outlet on the reservoir;

a conduit having a first end and a second end, the first end being connected to the inlet and the second end being connected to the outlet such that at least a portion of the sample of blood can flow through the conduit.

32. A method as defined in claim 27 wherein the step of collecting a sample comprises the step of holding the sample in a substantially optically clear flexible tube having a diameter less than about 3 mm.

33. A method as defined in claim 27 wherein the step of causing the sample to flow comprises the step of pumping the sample of blood using a roller pump.

34. A method as defined in claim 27 wherein the step of introducing an aggregating agent comprises the step of introducing an aggregating agent selected from the group consisting of: ADP, collagen, ristocetin, and epinephrine.

35. A method as defined in claim 27 wherein the step of illuminating comprises the step of illuminating the sample with electromagnetic radiation in the portion of the spectrum selected from the group consisting of: infrared, visible, and ultraviolet.

36. A method as defined in claim 27 wherein the step of illuminating comprises the step of illuminating the sample with electromagnetic radiation at about 830 nm.

37. A method as defined in claim 27 wherein the step of illuminating comprises the step of illuminating the sample with coherent light.

38. A method as defined in claim 27 wherein the step of detecting comprises detecting the scattered light with a photodetector.

39. A method as defined in claim 27 wherein the step of detecting comprises detecting the scattered light with at least a first photodetector and a second photodetector, the first and second photodetectors being positioned about the scattering volume opposite each other.

40. A method as defined in claim 27 wherein the step of detecting comprises detecting the scattered light with at least a first photodetector oriented at an angle greater than 70° with respect to a source of illumination.

41. A method as defined in claim 27 wherein the step of detecting comprises detecting the scattered light with at least a first photodetector oriented at an angle with respect to a source of illumination such that the light scattered by platelet aggregates in the sample of blood tends to be maximized.

42. A method as defined in claim 27 wherein the step of processing comprises processing the scattering signal with a microprocessor.

43. A method as defined in claim 27 wherein the step of displaying at least one platelet aggregation parameter comprises displaying at least one parameter selected from the group consisting of:

the number of platelet aggregates formed; and the size of the platelet aggregates formed.

44. A device for collecting and holding a sample of blood so that one or more characteristics of the sample can be assessed by an optical analysis apparatus, the device comprising:

a reservoir for holding the sample of blood;

means for allowing entry of the sample of blood from a device withdrawing blood from the patient and into the reservoir;

an inlet on the reservoir;

an outlet on the reservoir;

a conduit having a first end and a second end, the first end being connected to the inlet and the second end being connected to the outlet such that at least a portion of the sample of blood can flow through the conduit whereby optical analysis of the blood within the conduit can be carried out and the conduit can be operationally placed in and removed from the optical analysis apparatus.

45. A device as defined in claim 44 wherein the conduit comprises a substantially optically clear flexible tube.

46. A device as defined in claim 44 further comprising an anticoagulant in the interior of the reservoir.

47. A device as defined in claim 44 further comprising means for causing the blood to flow through the conduit.

48. A device as defined in claim 44 further comprising means for introducing a aggregating agent into the reservoir.

49. A device as defined in claim 44 further comprising:

means for causing flow of the blood through a scattering volume;

means for introducing an aggregating agent into the sample such that platelet aggregation occurs;

means for illuminating the blood within the scattering volume;

means for detecting the light scattered by the blood in the scattering volume and generating a scattering signal; and means for processing the scattering signal and displaying at least one platelet aggregation parameter in a humanly perceptible manner.

50. A device as defined in claim 44 wherein the at least one characteristics of the sample comprises characteristics selected from the group consisting of:

the number of platelet aggregates formed; and the size of the platelet aggregates formed.

* * * * *